(12) United States Patent
Willis et al.

(10) Patent No.: US 7,477,763 B2
(45) Date of Patent: Jan. 13, 2009

(54) COMPUTER GENERATED REPRESENTATION OF THE IMAGING PATTERN OF AN IMAGING DEVICE

(75) Inventors: N. Parker Willis, Atherton, CA (US); David L. McGee, Sunnyvale, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 997 days.

(21) Appl. No.: 10/318,474

(22) Filed: Dec. 13, 2002

(65) Prior Publication Data

US 2003/0231789 A1 Dec. 18, 2003

Related U.S. Application Data

(60) Provisional application No. 60/389,901, filed on Jun. 18, 2002.

(51) Int. Cl.
*G06K 9/00* (2006.01)

(52) U.S. Cl. .............................. 382/128; 128/922; 378/4

(58) Field of Classification Search ................. 128/922; 382/100, 128, 129, 130, 131, 132, 201, 206, 382/284, 294, 302; 378/4–27
See application file for complete search history.

(56) References Cited

U.S. PATENT DOCUMENTS

| | | | |
|---|---|---|---|
| 4,757,821 A | 7/1988 | Snyder | |
| 4,821,731 A | 4/1989 | Martinelli et al. | |
| 4,841,977 A | 6/1989 | Griffith et al. | |
| 4,945,478 A * | 7/1990 | Merickel et al. | 382/131 |
| 5,025,463 A * | 6/1991 | Saito et al. | 378/19 |
| 5,391,199 A | 2/1995 | Ben-Haim | |
| 5,406,951 A | 4/1995 | ten Hoff et al. | |
| 5,655,537 A | 8/1997 | Crowley | |
| 5,687,737 A | 11/1997 | Branham et al. | |
| 5,704,361 A | 1/1998 | Seward et al. | |
| 5,724,978 A | 3/1998 | Tenhoff | |
| 5,825,908 A * | 10/1998 | Pieper et al. | 382/131 |
| 5,842,473 A | 12/1998 | Fenster et al. | |
| 5,908,445 A | 6/1999 | Whayne et al. | |
| 5,938,602 A | 8/1999 | Lloyd | |
| 5,983,126 A | 11/1999 | Wittkampf | |
| 6,047,218 A | 4/2000 | Whayne et al. | |
| 6,146,390 A | 11/2000 | Heilbrun et al. | |

(Continued)

OTHER PUBLICATIONS

Yamashita, Juli, et al "Real-Time 3-D Model-Based Navigation System for Endoscopic Paranasal Sinus Surgery" IEEE Transactions on Biomedical Engineering, vol. 46, No. 1, Jan. 1999, pp. 107-116.

(Continued)

*Primary Examiner*—Anand Bhatnagar
(74) *Attorney, Agent, or Firm*—Vista IP Law Group LLP

(57) ABSTRACT

The present invention provides systems and methods for locating an imaging device within or outside of the body and for displaying a graphical representation of the imaging pattern associated with the imaging device within a global representation of the body. The imaging pattern characterizes the "field of vision" of the imaging device, and the graphical imaging pattern within the global representation of the body visually indicates the portion of the body that is being imaged by the imaging device in relation to the global representation of the body.

45 Claims, 23 Drawing Sheets

U.S. PATENT DOCUMENTS

| | | | |
|---|---|---|---|
| 6,159,152 | A | 12/2000 | Sumanaweera et al. |
| 6,216,027 | B1 | 4/2001 | Willis et al. |
| 6,224,556 | B1 | 5/2001 | Schwartz et al. |
| 6,248,075 | B1 | 6/2001 | McGee |
| 6,347,240 | B1 | 2/2002 | Foley et al. |
| 6,358,245 | B1 | 3/2002 | Edwards et al. |
| 6,364,840 | B1 | 4/2002 | Crowley |
| 6,429,861 | B1 | 8/2002 | Hossack et al. |
| 6,434,415 | B1 | 8/2002 | Foley et al. |
| 6,450,964 | B1 | 9/2002 | Webler |
| 6,473,635 | B1 | 10/2002 | Rasche |
| 6,490,467 | B1 | 12/2002 | Bucholz et al. |
| 6,490,474 | B1 | 12/2002 | Willis et al. |
| 6,491,702 | B2 | 12/2002 | Heilbrun et al. |
| 2001/0050969 | A1* | 12/2001 | Sembritzki et al. ............. 378/4 |
| 2002/0062062 | A1* | 5/2002 | Belson et al. ............... 600/146 |
| 2005/0018892 | A1* | 1/2005 | Pieper et al. ................ 382/131 |
| 2005/0228250 | A1* | 10/2005 | Bitter et al. ................. 600/407 |

OTHER PUBLICATIONS

Weidenbach, M, et al "Augmented Reality Simulator for Training in Two-Dimensional Echocardiography" Computers and Biomedical Research, Academic Press, London, GB, vol. 33, No. 1, Feb. 200, pp. 11-22, 2000.

Berlage, T., "Augmented-Reality Communication for Diagnostic Tasks in Cardiology" IEEE Transactions on Information Technology in Biomedice, IEEE Service Center, Piscataway, NJ, US, vol. 2, No. 3, Sep. 1998, pp. 169-173.

Dey, Damini, et al, "Automatic Fusion of Freehand Endoscopic Brain Images to Three-Dimensional Surfaces: Creating Stereoscopic Panoramas" IEEE Transactions on Medical Imaging, IEEE Inc. New York, US, vol. 21, No. 1, Jan. 2002, pp. 23-30.

Martin, Roy, et al, "An Endoscopic Micromanipulator for Multiplanar Trasesophageal Imaging" Ultrasound in Medicine and Biology, New York, NY, US, vol. 12, No. 12, Dec. 1986, pp. 965-975.

Kosaka, Akio, et al, "Augmented Reality System for Surgical Navigation Using Robust Target Vision", Proceedings 2000 IEEE Conference on Computer Vision and Patter Recognition. CVPR 2000. Hilton Head Island, SC, Jun. 2000, vol. 2 of 2, pp. 187-194.

\* cited by examiner

COMPUTER GENERATED REPRESENTATION OF THE IMAGING PATTERN OF AN IMAGING DEVICE

RELATED APPLICATIONS

The present application claims benefit of U.S. Provisional Patent Application No. 60/389,901, filed Jun. 18, 2002, which is hereby fully and expressly incorporated herein by reference.

FIELD OF THE INVENTION

The invention relates generally to imaging devices and more particularly to systems and methods for imaging body tissue.

BACKGROUND OF THE INVENTION

For purposes of diagnosis and treatment planning, imaging techniques are commonly used in medical procedures to view the internal anatomy of a patient's body. In one imaging technique, an ultrasound device with one or more ultrasound transducers mounted on its tip is inserted into the patient's body, e.g., through a blood vessel. To obtain an interior image of the body, the ultrasound transducer emits pulses of ultrasound energy into the body. A portion of the ultrasound energy is reflected off of the internal anatomy of the body back to the transducer. The reflected ultrasound energy (echo) impinging on the transducer produces an electrical signal, which is used to form the interior image of the body. To provide a planar or sector view of the surrounding tissue, the ultrasound device will typically have either one or more rotating transducers or a phased array of transducers that are mechanically disposed about the circumference or along the axis of the ultrasound device.

In order to assist physicians in maneuvering medical devices (e.g., imaging devices) to sites of interest in the body, several guidance systems have been developed. In one guidance system, a fluoroscopic image of the device (or at least the radiopaque bands of the device) and surrounding anatomical landmarks (with or without the use of contrast media) in the body are taken and displayed to the physician. The fluoroscopic image enables the physician to ascertain the position of the device within the body and maneuver the device to the site of interest. In another guidance system using anatomic mapping, a graphical representation of the device or portion of the device is displayed in a 3-D computer-generated representation of a body tissue, e.g., heart chamber. The 3-D representation of the body tissue is produced by mapping the geometry and/or electrical activity of the inner surface of the body tissue in a 3-D coordinate system by moving a mapping device to multiple points on the body tissue. The position of the device to be guided within the body tissue is determined by placing one or more location sensors on the device and tracking the position of these sensors within the 3-D coordinate system. An example of this type of guidance system is the Realtime Position Management™ (RPM) tracking system developed commercially by Cardiac Pathways Corporation, now part of Boston Scientific Corp. The RPM system is currently used in the treatment of cardiac arrhythmia to define cardiac anatomy, map cardiac electrical activity, and guide an ablation catheter to a treatment site in a patient's heart.

Although the utility of present guidance techniques for guiding devices to sites of interest in the body has been proven, they are limited in their ability to localize the specific body tissue that is being imaged by imaging devices at any given instant. As a result, it is difficult for physicians to determine what portion of the body he or she is imaging with imaging devices or to determine the location of those imaging devices relative to the patient's anatomy using present localization techniques.

SUMMARY OF THE INVENTION

The present inventions provide systems and methods for displaying a graphical representation of an imaging pattern associated with a local imaging device within a global representation of the body or a portion thereof.

In accordance with the present inventions, a local image of body tissue is generated using a local imaging device having an imaging pattern associated therewith. The local image can be generated in a variety of ways. For example, the local image can be generated internally using an ultrasound or optical catheter, or externally using an external ultrasound imaging device. In generating the local image, the image device may have one or more imaging devices, such as, e.g., an optical lens, a single rotating ultrasound transducer, or an array of ultrasound transducers. The system may further comprise local imaging control/processing circuitry for processing and generating the local image, and a display for displaying the local image to the physician. In any event, the broadest aspects of the inventions should not be limited to the particular manner and means for generating the local image. The importance is that the local image allows the physician to closely examine a region of interest within the body tissue.

The present inventions further include generating a global representation of the body tissue. As with the local image, the global representation of the body can be generated in a variety of ways. For example, the global or regional representation can be generated by graphically reconstructing the body tissue, or using standard imaging modalities, such as, e.g., ultrasound, MRI, or fluoroscopy. Again, the broadest aspects of the inventions should not be limited to the particular manner and means for generating the global representation. The importance is that the global representation provides spatial context for the local image.

The present inventions further include generating a graphical image of the imaging pattern. Depending on the arrangement of the imaging element(s), the imaging pattern may take on a variety of forms, e.g., conically-shaped or sector shaped. The imaging pattern of the particular imaging device may be pre-stored in the system or may be entered by the physician.

The present inventions further include generating a composite image comprising the graphical imaging pattern and the global representation. The graphical imaging pattern within the composite image visually indicates the imaging pattern of the imaging device and the portion of the body that is being imaged by the imaging device in relation to the global representation of the body. The graphical imaging pattern can be positioned in the composite image in a variety of ways.

For example, the position of the imaging element(s) from which the imaging pattern originates can be determined in a two or three-dimensional coordinate system, e.g., by locating one or more location elements on the imaging device and determining the position of the imaging element(s) based on the determined positions of the location element(s) within the coordinate system. If the global representation is generated using a standard imaging modality, the global representation can be registered within the coordinate system, thereby aligning the positions of the imaging element(s), and thus, the origin of the imaging pattern, with the global representation within the coordinate system. If the global representation is generated by graphical reconstruction, the global representation will typically already be registered within the same coordinate system in which the position of the imaging element(s) is determined. Alternatively, rather than locating the imaging element(s) within a coordinate system, location elements locating within the global representation itself. For example, the imaging device can carry radiopaque markers that show up on a global fluoroscopic image.

The imaging pattern can also be oriented within the composite image by determining the orientation of the imaging elements(s). This can be accomplished by, e.g., determining the orientation of an adjacent location element, if such location element provides orientation data, or by determining the orientation of the imaging device based on the locations of multiple location elements and the known geometry of the imaging device.

The local and composite images can be displayed on separate displays or on the same display for visualization by the physician.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
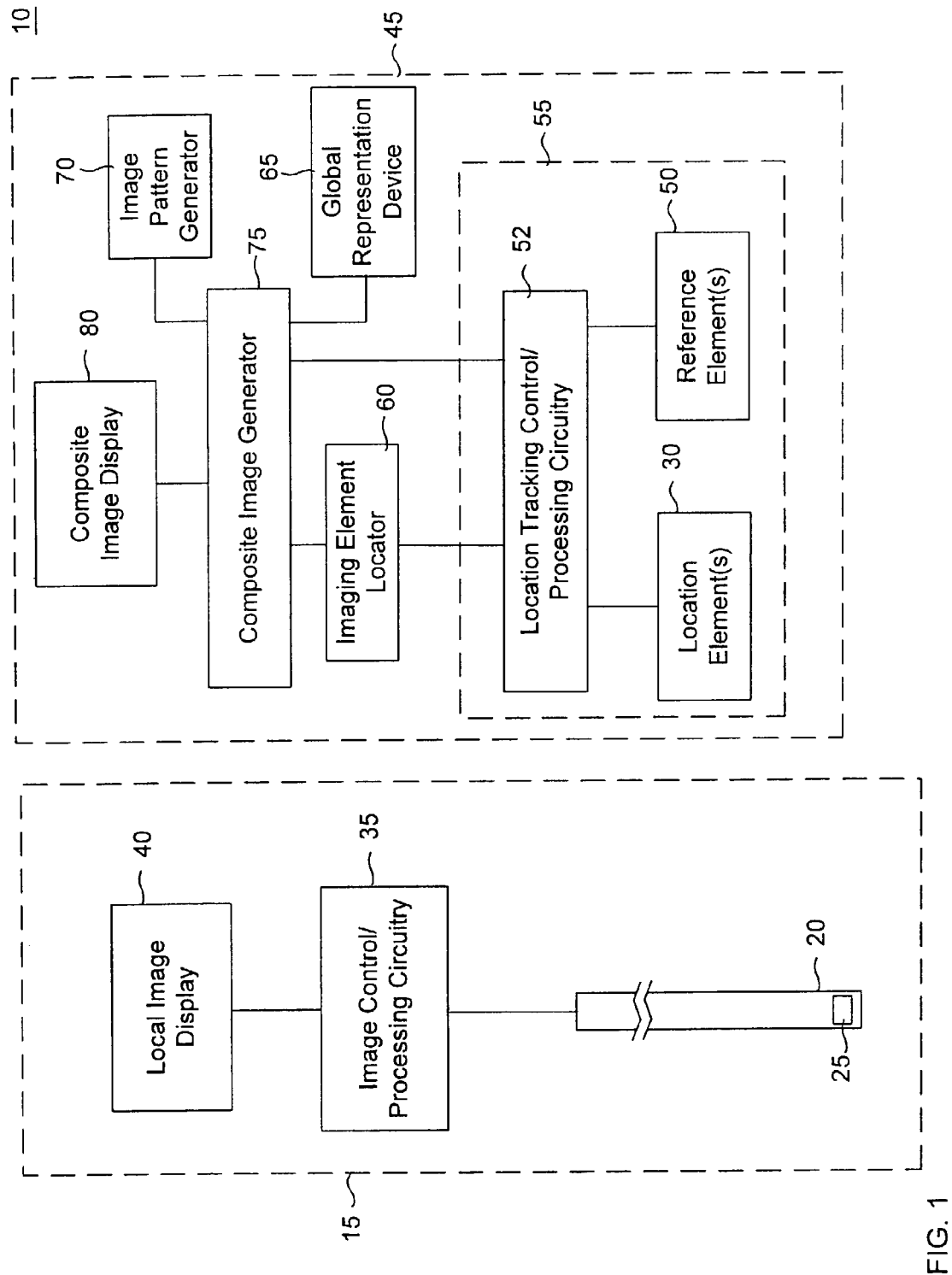
FIG. 1 is a functional block diagram of one preferred embodiment of a body tissue imaging system constructed in accordance with the present inventions.

FIG. 1 illustrates the components of an exemplary body tissue imaging system 10 according to one embodiment of the present invention. The system 10 includes a local imaging subsystem 15 for imaging and displaying a local region of the body tissue. The local imaging subsystem 15 comprises a peripheral imaging device 20, local image control/processing circuitry 35 coupled to the imaging device 20, and a local image display 40 coupled to the image control/processing circuitry 35. The imaging device 20 may be constructed for insertion into the body, e.g., a catheter that can be introduced through the esophagus or a blood vessel, to image the interior of the body. The imaging device 20 may also be an external imaging device that images the interior of the body from a position outside the body. The imaging device 20 comprises an imaging element 25, e.g., a rotating ultrasound imager, a phased array ultrasound imager, an optical imager, e.g., Optical Coherence Tomography (OCT) imager, or the like. The imaging element 25 produces and/or detects signals, e.g., electrical or optical signals, representing the interior of the body and outputs these signals to the image control/processing circuitry 35. The image control/processing circuitry 35 processes these signals into local interior images of the body and displays the interior images on the image display 40.

The system 10 further includes a guidance subsystem 45 for guiding the imaging device 20 and displaying a graphical representation of the imaging device 20 and its imaging pattern within a global representation of the body. The guidance subsystem 45 comprises a location tracking subsystem 55 for tracking the position and/or orientation of the imaging device 20 in a 3-D coordinate system. The location tracking subsystem 55 further includes one or more reference element(s) 50, one or more location element(s) 30, which are carried by the imaging device 20, and location tracking control/processing circuitry 52 coupled to the reference element(s) 50 and the location element(s) 30. The reference element(s) 50 establish a 3-D coordinate system in which the tracking control/processing circuitry 52 tracks the positions of the location element(s) 30, which are located on the imaging device 20, as explained further below.

The guidance subsystem 45 also comprises an imaging element locator 60 coupled to the tracking control/processing circuitry 52. The imaging element locator 60 determines the position, and optionally the orientation and/or geometry, of the imaging element 25 in the 3-D coordinate system based on the tracked positions of the location elements 30 and the relative position of the imaging element 25 to the location elements 30.

The guidance subsystem 45 further comprises a global representation device 65. The global representation device 65 produces a global representation of the body tissue within which the imaging device 20 is to be guided and/or within which the imaging pattern of the device 20 is to be depicted. It should be noted that for the purposes of this specification, the term "representation" means any representation that allows a physician to visualize a representation of the body tissue or relevant structures. Thus, the global representation of the body tissue may, for example, take the form of a MRI, ultrasound image, fluoroscopic image, or graphical representation of the body tissue. Preferably, the global representation of the body tissue is registered with the 3-D coordinate system established by the reference element(s) 50.

The guidance subsystem 34 further comprises an image pattern generator 70, which generates a graphical representation of the imaging pattern associated with the imaging device 20. The guidance subsystem 34 further comprises a composite image generator 75, which is coupled to the tracking control/processing circuitry 52, the location element locator 60, the global representation device 65, and the image pattern generator 70. The composite image generator 75 generates a composite image comprising a graphical representation of the imaging device 20 and its associated imaging pattern within the global representation of the body tissue. The composite image generator 75 positions the graphical representation of the imaging device 20 within the composite image based on geometry of the imaging device 20 given by the imaging element locator 60. In addition, the composite image generator 75 positions the graphical representation of the associated imaging pattern within the composite image based on the determined position and orientation of the imaging element 25 given by the imaging element locator 60. Alternatively, the imaging pattern, but not the imaging device 20, is graphically represented. The graphical representation of the imaging pattern within the composite image visually indicates the portion of the body that is being imaged by the imaging device 20 in relation to the global representation of the body tissue. The composite image is displayed on a composite image display 80, e.g., a video monitor.

It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

1. Local Imaging Subsystem

Figure 2:
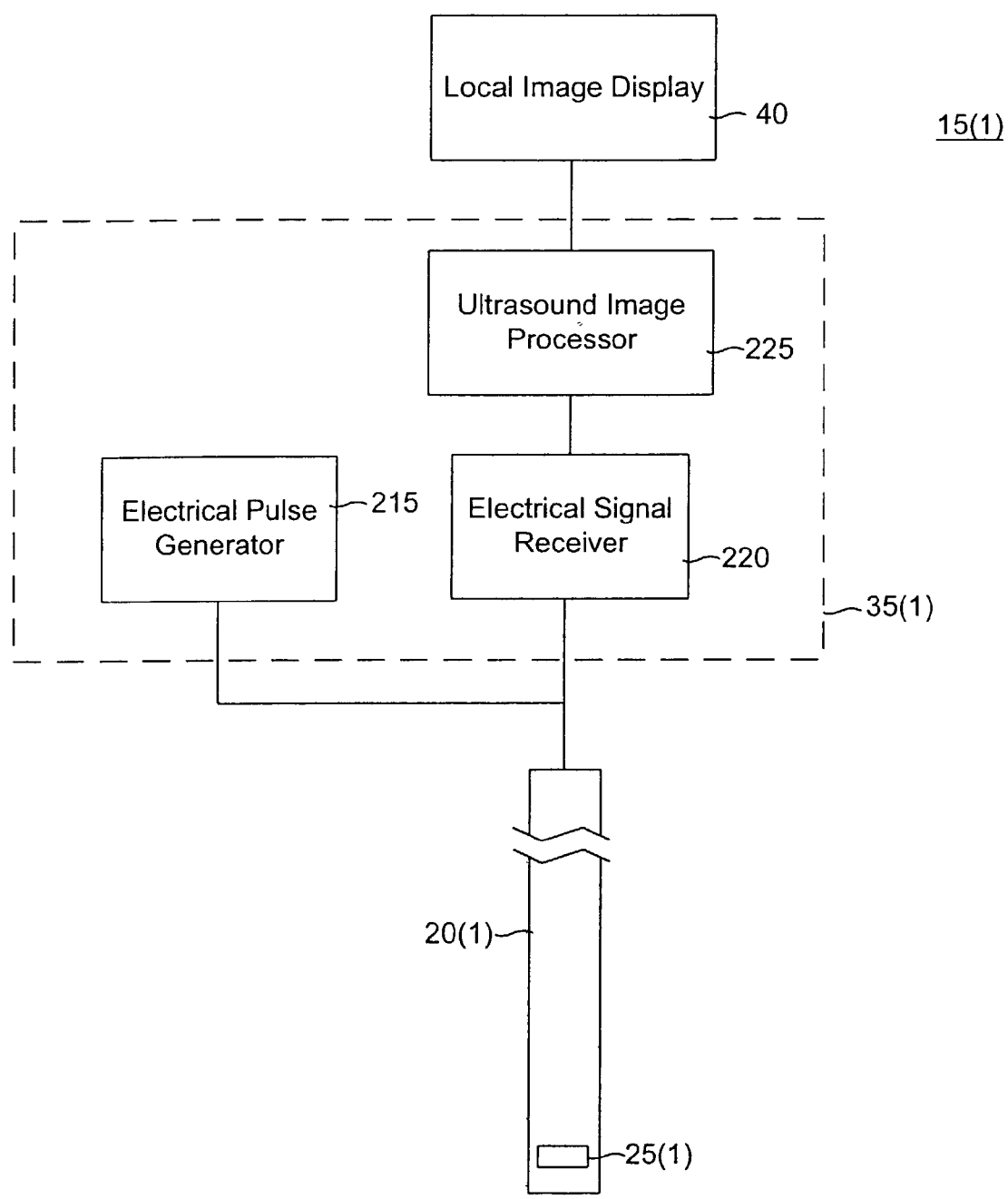
FIG. 2 is a functional block diagram of an ultrasound-based local imaging subsystem that may be used in the body tissue imaging system of FIG. 1.

FIG. 2 illustrates an ultrasound-based local imaging subsystem 15(1) according to one embodiment of the invention, in which the imaging element 25 takes the form of an ultrasound imaging device 20(1) and the imaging element(s) 25 takes the form of one or more ultrasound transducer(s) 25(1). The ultrasound transducer(s) 25(1) may be rotated within the imaging device 20(1) by a drive shaft coupled to a drive motor (not shown) in order to obtain cross-sectional images (i.e. "slices") of the body. Alternatively, the ultrasound transducer(s) 25(1) may be arranged in a one-or-two dimensional phased array on the imaging device 20(1) for imaging a plane and/or sector of the body. The local image control/processing circuitry 35(1) further includes an electrical pulse generator 215 and an electrical signal receiver 220, both of which are coupled to the ultrasound transducer(s) 25(1). The ultrasound image control/processing circuitry 35 further includes an ultrasound image processor 230 coupled to the electrical signal receiver 220.

To obtain an ultrasound image of the interior of the body, the imaging device 20(1) may be inserted into the body or placed on the skin surface of the body with the ultrasound transducer(s) 25(1) directed towards the interior of the body. The pulse generator 215 transmits electrical pulses to excite the ultrasound transducer(s) 25(1). The transducer(s) 25(1) convert the electrical pulses into pulses of ultrasound energy, which are emitted in the body. A portion of the ultrasound energy is reflected off of the internal anatomy of the body back to the transducer(s) 25(1). The transducer(s) 25(1) convert the back-reflected ultrasound energy into electrical signals representing the interior of the body. The electrical signals are detected by the electrical signal receiver 220 and outputted to the ultrasound image processor 230, which processes the received electrical signals into an ultrasound image of the body using known ultrasound image processing techniques. The electrical signal receiver 220 may amplify and/or filter the electrical signals before outputting them to the ultrasound image processor 230. The ultrasound image processor 230 displays the ultrasound image on the local image display 40.

Figure 3A:
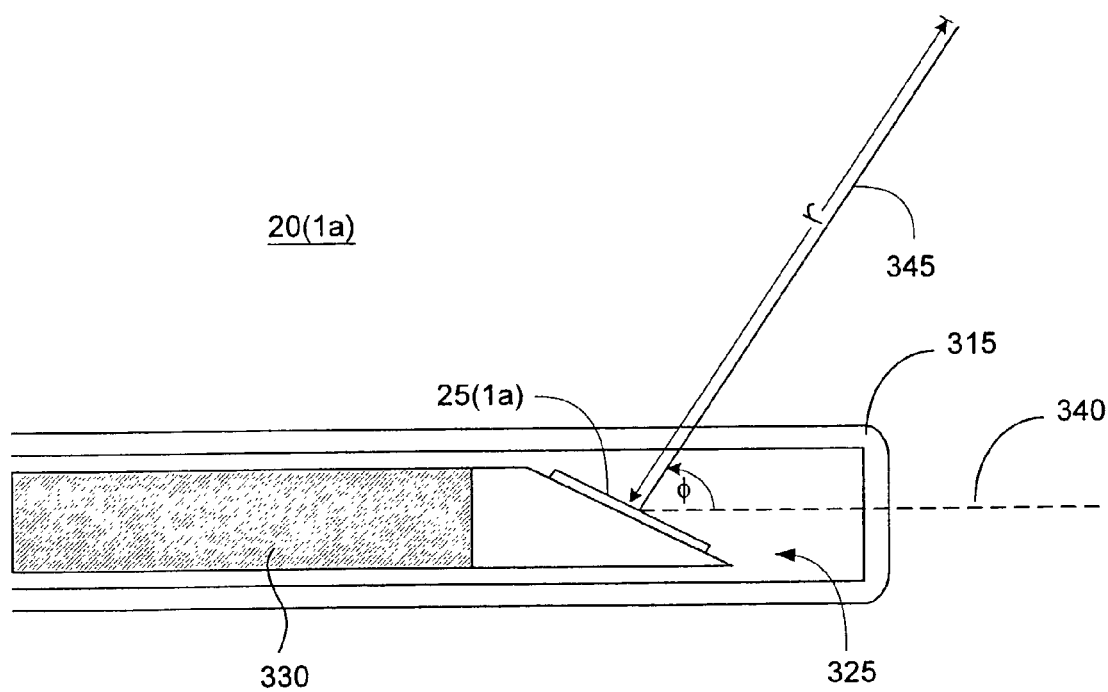
FIG. 3A is a cross-sectional view of an ultrasonic imaging device that may be used in the ultrasound-based local imaging subsystem of FIG. 2, wherein the ultrasonic catheter carries a single rotating ultrasound transducer.

FIG. 3A illustrates an axial cross-sectional view of an embodiment of an ultrasonic imaging device 20(1a), in which the ultrasound transducer(s) 25(1) takes the form of a rotating ultrasound imaging transducer 25(1a). The imaging device 20(1a) comprises an elongated catheter body or sheath 315 having a lumen 325 extending therethrough. The catheter body 315 is made of a flexible material so that it is able to bend along the path of a body lumen. The imaging device 20(1a) further includes a drive shaft 330 extending through the lumen 325. The rotating ultrasound imaging transducer 25(1a) is mounted on the distal end of the drive shaft 330. The catheter body 315 includes an acoustic window (not shown) for allowing ultrasound pulses to pass through the catheter body 315. The lumen 325 may be filled with fluid, e.g., water, to better couple ultrasound energy from the ultrasound transducer 25(1a) to the surrounding body.

To obtain an interior cross-sectional image of the body, the imaging transducer 25(1a) is mechanically rotated one revolution (360 degrees) along its axis 340 while simultaneously emitting ultrasound pulses at different angular directions in the body. The ultrasound image processor 230 processes the electrical signals received during one revolution of the ultrasound transducer 25(1a) to construct the cross-sectional image of the body. The local imaging subsystem 35(1) may continuously update the ultrasound image to provide a real-time image of the body.

To image a three-dimensional volume of the body, the ultrasound transducer 25(1a) may be slid axially within the catheter body 315 by pulling back the drive shaft 330 with a drive motor (not shown). Alternatively, the entire catheter body 315, with the ultrasound transducer 25(1a) can be pulled back. As the transducer 25(1a) is slid axially, the ultrasound transducer 25(1a) is rotated to obtain multiple cross-sectional images (i.e., "slices") of the body at different positions within the body. The ultrasound image processor 230 then aggregates (i.e., pieces together) the multiple cross-sectional images to reconstruct the volume of the body using known volume reconstruction techniques.

An alternative method for imaging a three-dimensional volume would be to move the entire catheter along a path rather than slide the ultrasound transducer within the catheter itself.

Figure 3B:
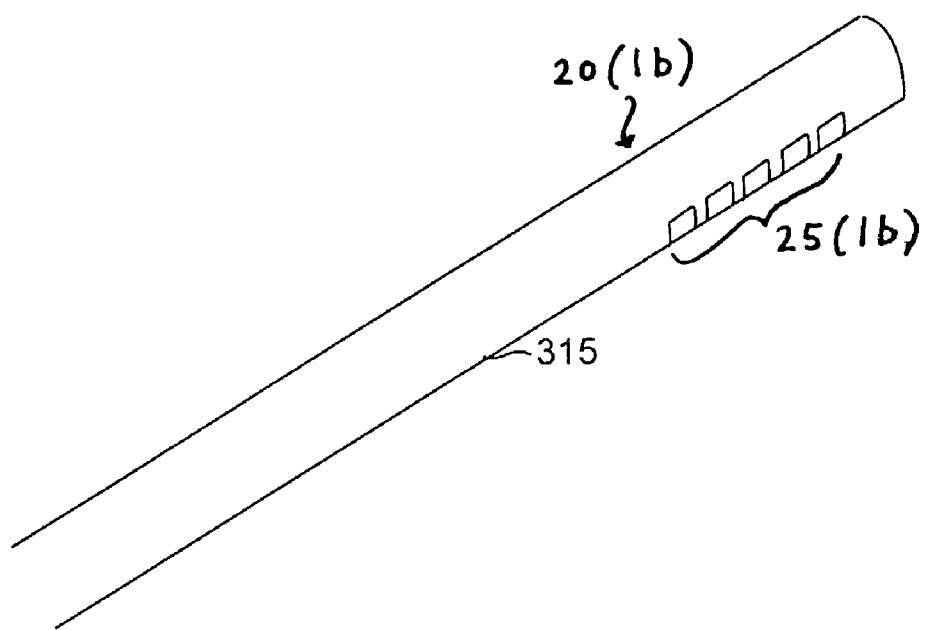
FIG. 3B is a perspective view of an ultrasonic imaging device that may be used in the ultrasound-based local imaging subsystem of FIG. 2, wherein the ultrasonic catheter carries a phased array of ultrasound transducers.

FIG. 3B illustrates another embodiment of the ultrasonic imaging device 20(1b), in which the ultrasound transducer(s) 25(1) takes the form of a one-or-two dimensional imaging transducer array 25(1b). The imaging device 20(1b) comprises an elongated catheter body or sheath 315 with the transducers of the transducer array 25(1b) disposed along the axis (as shown in FIG. 3B) or about the circumference on the catheter body 315. The transducer array 25(1b) images a plane and/or sector of the body. An advantage of the transducer array 25(1b) is that its ultrasonic beam can be electronically steered (i.e., deflected) and/or focused by individually controlling the phase or delay of each transducer of the array 25(1b), e.g., using delay elements (not shown). As a result, the transducer array 25(1b) is able to electronically scan the body and obtain faster scan rates than a mechanical scanner, e.g., the rotating transducer 25(1a).

Figure 3C:
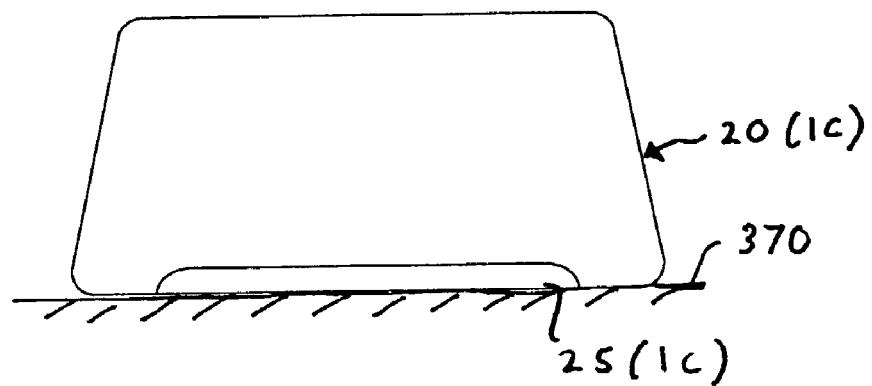
FIG. 3C is a plan view of an external ultrasonic imaging device that may be used in the ultrasound-based local imaging subsystem of FIG. 2.

FIG. 3C illustrates still another embodiment of an external ultrasonic imaging device 20(1c), in which the ultrasound transducers 25(1) takes the form of a one-or-two dimensional transducer array 25(1c). To obtain a planar or sector image of the interior of the body, the external imaging device 20(1c) is placed on the skin surface 370 of the body with the transducer array 25(1c) directed towards the interior of the body. This type of ultrasonic imaging device 20(1c) is well known and commonly used to image a fetus in the womb as part of prenatal care.

Figure 4:
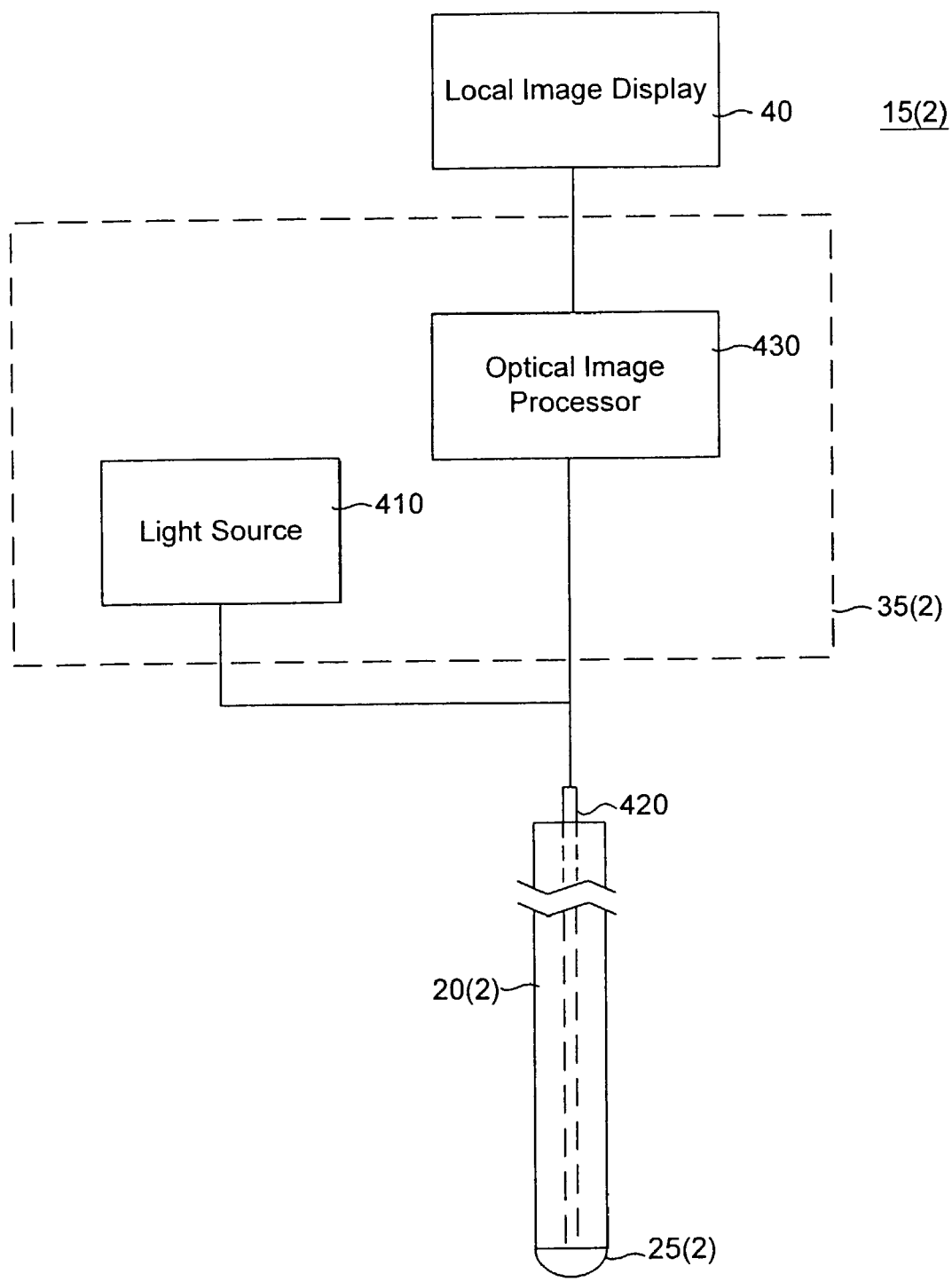
FIG. 4 is a functional block diagram of an optical-based local imaging subsystem that may be used in the body tissue imaging system of FIG. 1.

FIG. 4 illustrates an optical-based local imaging subsystem 15(2) according to one embodiment of the invention. The local imaging subsystem 15(2) comprises local image control/processing circuitry 35(2), and an associated optical imaging catheter 20(2) with an optical imaging lens 25(2) and optical fiber 420 extending therethrough. The image control and/processing circuitry 35(2) includes a light source 410, e.g., a laser, and an optical image processor 430. The optical fiber 420 is optically coupled at its distal end to the lens 25(2) and at its proximal end to both the light source 410 and the optical image processor 430.

To obtain an optical image of the interior of the body, the optical imaging catheter 20(2) is inserted into the body to a site of interest in the body. The optical fiber 420 transmits light (or other form of radiation) from the source 410 to the imaging lens 25(2), which emits the light in the body. A portion of the light is reflected off of the internal anatomy of the body back to the lens 25(2), which couples the received back-reflected light to the optical fiber 420. The optical fiber 420 transmits the back-reflected light to the optical image processor 430, which processes the back-reflected light into an interior image of the body using known techniques and displays the interior image of the body on the local image display 40.

2. Location Tracking Subsystem

The location tracking subsystem 55 tracks the positions of the location elements 30 of the imaging device 20 within the three-dimensional coordinate system.

Figure 5:
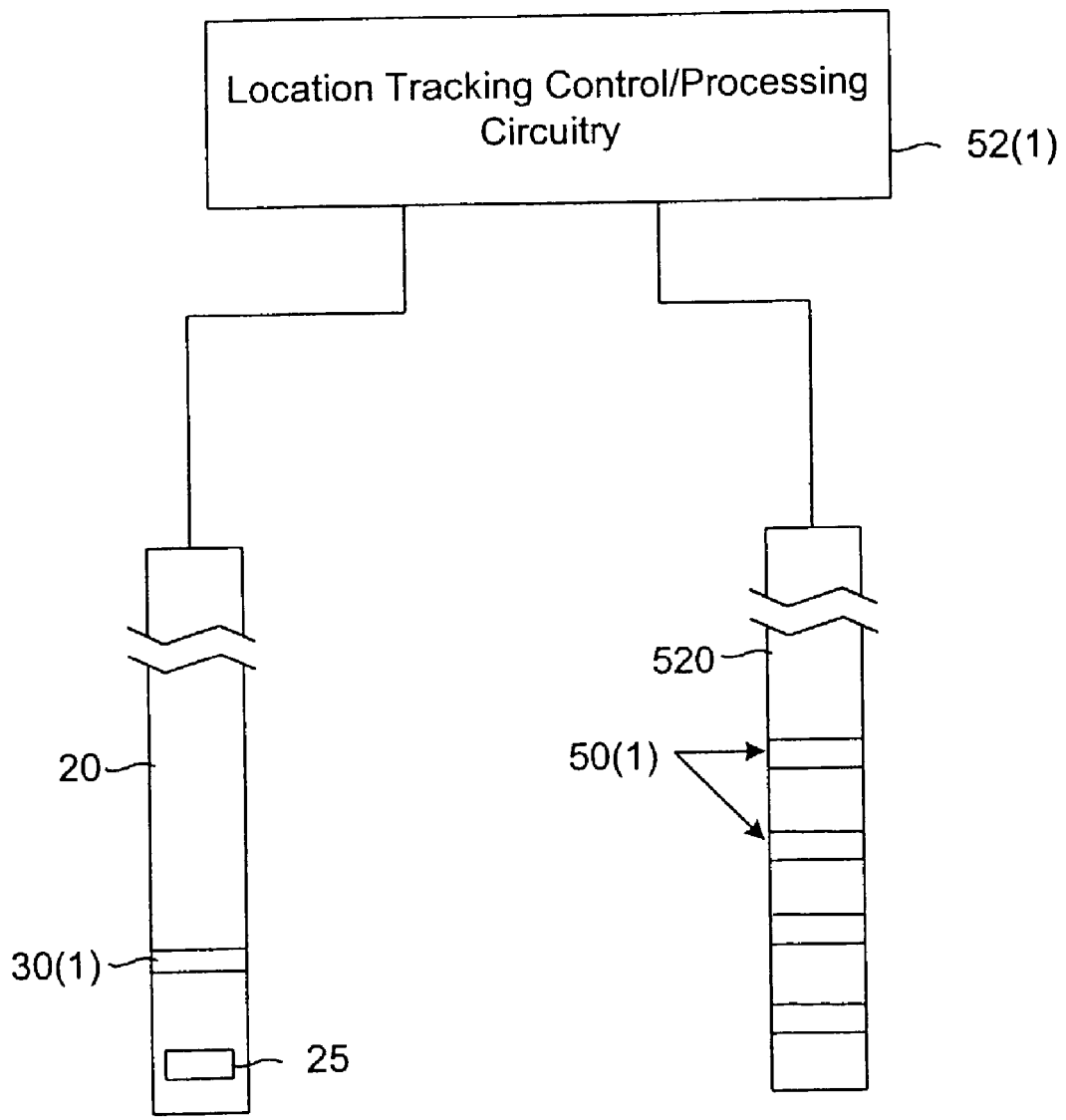
FIG. 5 is a functional block diagram of an ultrasound-based location tracking subsystem that may be used in the body tissue imaging system of FIG. 1.

FIG. 5 illustrates an embodiment of a location tracking subsystem 55(1) employing an ultrasonic tracking technique. The location tracking subsystem 55(1) comprises ultrasound tracking control/processing circuitry 52(1), four or more reference ultrasound transducers 50(1), and two or more ultrasound location transducers 30(1) located on the imaging device 20. Preferably, the location transducers 30(1) are placed along different positions on the imaging device 20. The tracking control/processing circuitry 52(1) causes the reference transducers 50(1) and location transducers 30(1) to transmit and receive ultrasound pulses (e.g., 500 KHz pulses) to each other. The reference transducers 50(1) may be located, e.g., one or more a reference catheter(s) 520 for placement inside the body, as shown in FIG. 5. Alternatively, the reference transducers 50(1) may be placed outside of the body or on the patient's skin. Each of the location transducers 30(1) is capable of detecting ultrasound pulses emitted from the reference transducers 50(1).

To establish a 3-D coordinate system, the reference transducers 50(1) are located within or outside of the body, and the reference transducers 50(1) transmit ultrasound pulses to each other. The tracking control/processing circuitry 52(1) calculates the relative distances between the reference transducers 50(1) using the "time of flight" and velocity of the ultrasound pulses between the reference transducers 50(1). The tracking control/processing circuitry 52(1) then triangulates the relative positions of the reference transducers 50(1) based on the distance calculations in order to establish the 3-D coordinate system. To track the positions of the location transducers 30(1) of the imaging device 20 in the 3-D coordinate system, the tracking control/processing circuitry 52(1) has each of the reference transducers 50(1) emit ultrasound pulses, which are detected by the location transducers 30(1) on the imaging device 20. The tracking control/processing circuitry 52(1) then computes the distance of each location transducers 30(1) from each of the reference transducers 50(1) using the "time of flight" and velocity of the detected ultrasound pulses. To simplify the distance computations, the velocity of the ultrasound pulses may be assumed to be constant. This assumption typically only produces a small error when the imaging device 20 is located inside the body since the velocity of ultrasound pulses varies little in body tissue and blood. Once the distance of the location transducers 30(1) from each of the reference transducers 50(1) is computed, the tracking control/processing circuitry 52(1) triangulates the positions of the location transducers 30(1) in the 3-D coordinate system. Preferably, the tracking control/processing circuitry 52(1) triangulates the positions of the location transducers 30(1) continually and in real time. Additional details on this type of tracking technique can be found in U.S. patent application Ser. No. 08/905,090, entitled "System for Electrode Localization Using Ultrasound," and U.S. patent application Ser. No. 09/128,304, entitled "A dynamically alterable three-dimensional graphical model of a body region," which are fully and expressly incorporated herein by reference.

To prevent or minimize ultrasound interference that may otherwise result from the transmission of ultrasound energy from an ultrasound imaging element, such as imaging element 25(1a), the tracking control/processing circuitry 52(1) preferably includes filtering circuitry. For example, the emission of ultrasound energy from the imaging element 25(1a) may cause the measured distance between a reference transducer 50(1) and a location transducer 30(1) to be less than it actually is. To minimize this adverse effect, multiple distance measurements between each combination of transducers can be taken for each measurement cycle. The greatest distance measurement can then be selected from the multiple distance measurements to obtain the true measurement between the transducers. Such a filtering technique is disclosed in U.S. patent application Ser. No. 10/213,441, entitled "Performing Ultrasound Ranging in the Presence of Ultrasound Interference," which is fully and expressly incorporated herein by reference.

Figure 6:
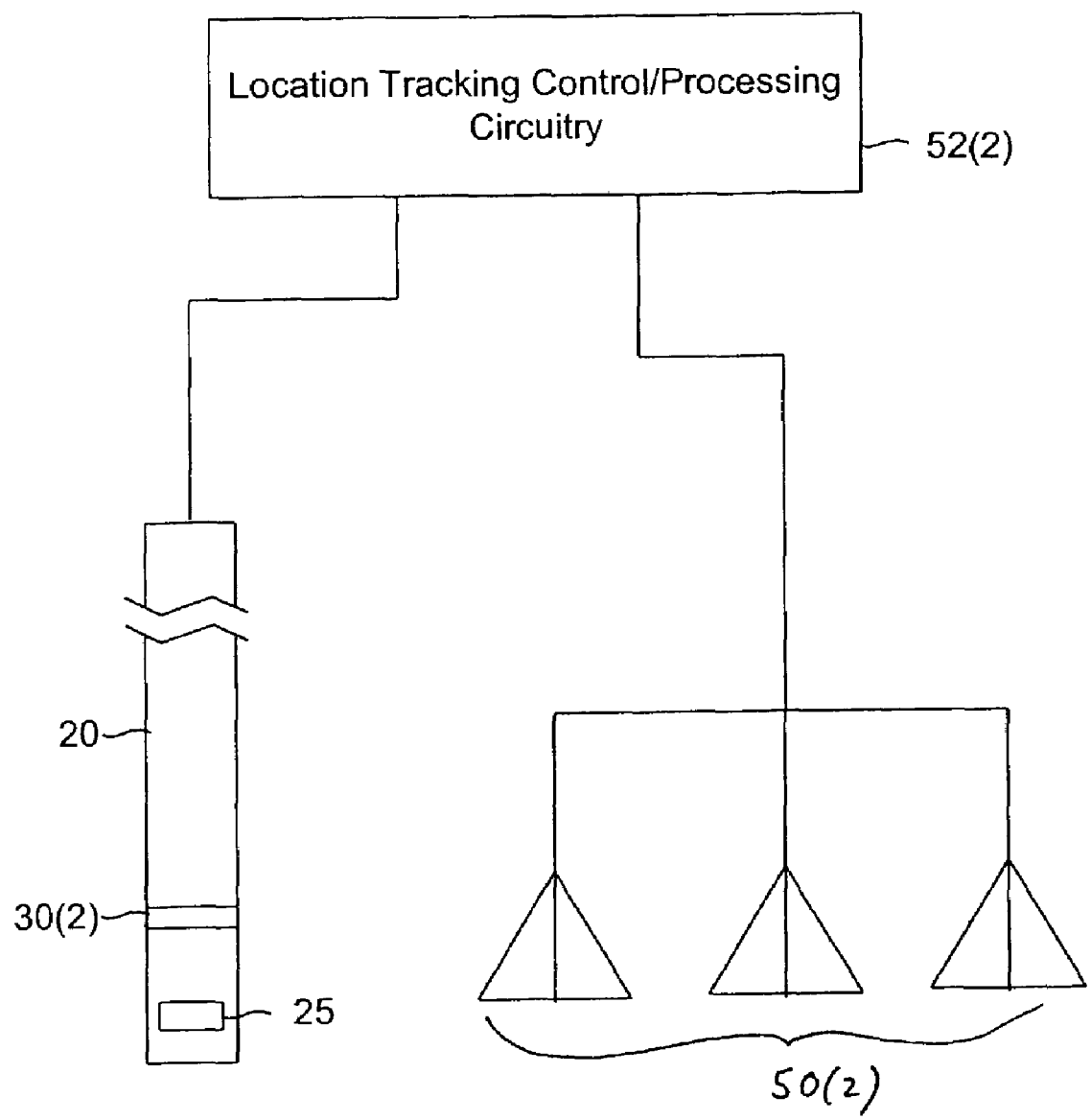
FIG. 6 is a functional block diagram of a magnetically-based location tracking subsystem that may be used in the body tissue imaging system of FIG. 1.

FIG. 6 illustrates an embodiment of a location tracking subsystem 55(2) employing a magnetic tracking technique. The location tracking subsystem 55(2) comprises magnetic tracking control/processing circuitry 52(2), three antennas 50(2), and one or more magnetic location arrays 30(2) located on the imaging device 20. Each magnetic location 30(2) array comprises three or more closely spaced magnetic field strength sensors (e.g., magnetic sensor coils).

To establish a 3-D coordinate system, the antennas 50(2) are located within or outside of the body. The tracking control/processing circuitry 52(2) causes the antennas 50(2) to transmit three orthogonal magnetic fields that define the 3-D coordinate system. To track the positions of the magnetic location arrays 30(2) in the 3-D coordinate system, each one of the magnetic field sensors in the arrays 30(2) measures the strength of each of the orthogonal magnetic fields from its respective location. The tracking control/processing circuitry 52(2) uses the magnetic field strength measurements to compute distance vectors between the magnetic location arrays 30(2) and the centers of the antennas 50(2). The tracking control/processing circuitry 52(2) then deconstructs the distance vectors into their x, y, and z components in order to compute the position and orientation of each magnetic location array in the 3-D coordinate system. Optionally, at least one of the magnetic location arrays 30(2) comprises six or more magnetic field sensors 30(2), so that the tracking control/processing circuitry 52(2) may further deconstruct the distance vectors for the respective magnetic location array 30(2) into pitch, roll, and yaw data for the magnetic location array 30(2) in the 3-D coordinate system. Additional details on this type of tracking technique can be found in U.S. Pat. No. 5,391,199 to Ben-Haim, entitled "Apparatus and Method for Treating Cardiac Arrhythmias," which is fully and expressly incorporated herein by reference.

Figure 7:
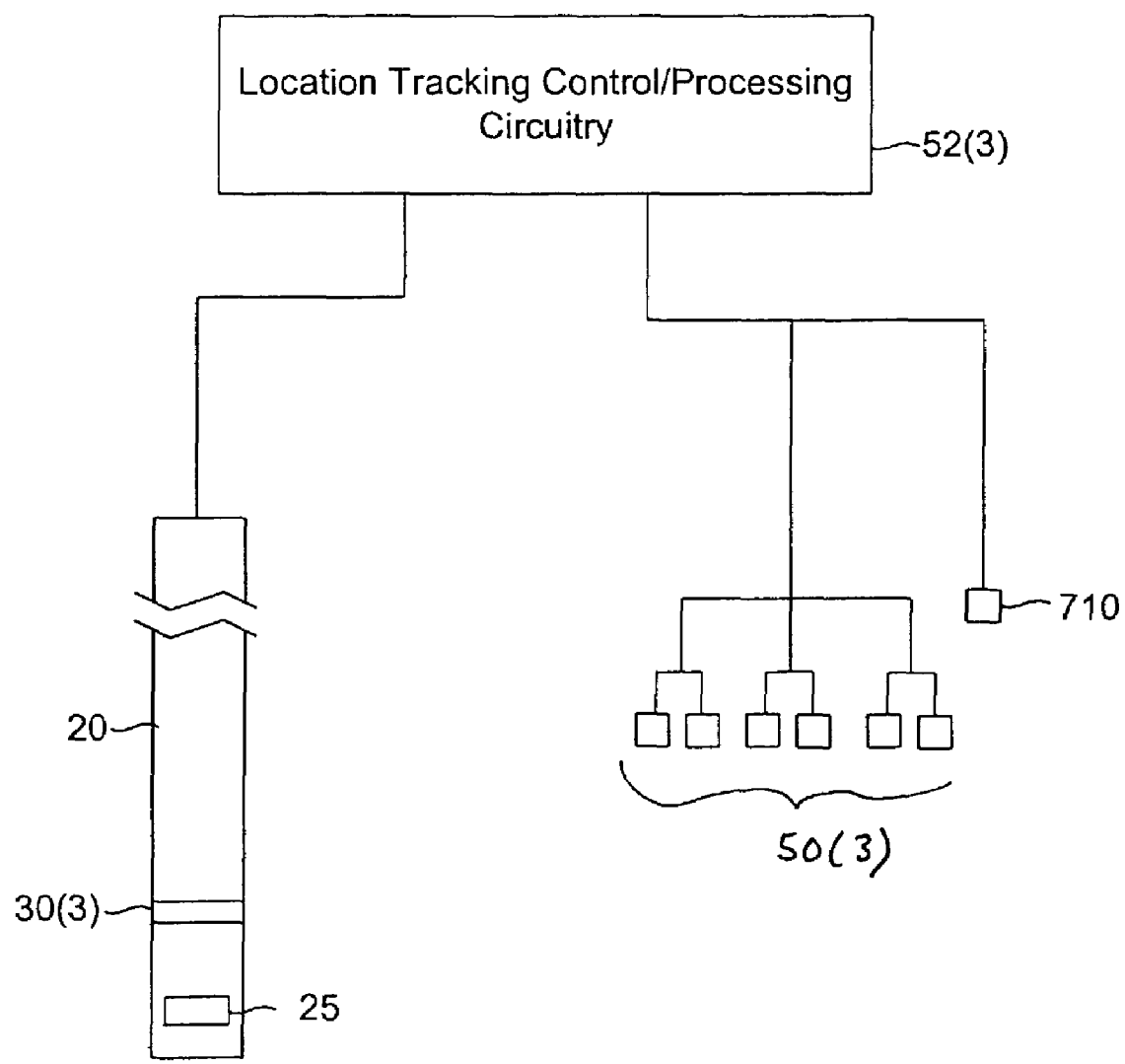
FIG. 7 is a functional block diagram of a voltage-based location tracking subsystem that may be used in the body tissue imaging system of FIG. 1.

FIG. 7 illustrates an embodiment of a location tracking subsystem 55(3) employing a voltage-based tracking technique. The location tracking subsystem 55(3) comprises a voltage tracking control/processing circuitry 52(3), three electrode pairs 50(3), a reference potential electrode 710, and one or more location electrodes 30(3) located on the imaging device 20.

To establish a 3-D coordinate system, the three electrode pairs 50(3) are placed on the patient's skin in mutually orthogonal directions, which define the x, y, and z direction of the 3-D coordinate system. For example, one electrode pair 50(3) may be placed in the direction from chest to back, a second electrode pair 50(3) in the direction from head to feet, and the third electrode pair 50(3) in the direction from left to right. In addition, the reference potential electrode 710 is placed on the patient's skin in order to establish a reference potential. The tracking control/processing circuitry 52(3) drives current into the three electrode pairs 50(3) to transmit three orthogonal alternating currents across the patient's body. In order to distinguish the three orthogonal currents from one another, the three currents may be given slightly different frequencies and/or phases, or may be sequenced in time.

To track the position of the imaging device 20 in the 3-D coordinate system, the location electrode 30(3) measures a voltage (i.e. potential) in the body associated with each of the three orthogonal currents flowing across the body and outputs the voltage measurements to the tracking control/processing circuitry 52(3). The voltage value associated with each current indicates the relative distance between the location electrode 30(3) and the corresponding electrode pair 50(3). The tracking control/processing circuitry 52(3) references the voltage measurements to the reference potential established by the reference electrode 710. The tracking control/processing circuitry 52(1) then computes the x, y, and z coordinates of the location electrode 30(3) in the 3-D coordinate system using the referenced voltage measurements and a calibration method employing two electrodes separated by a known interelectrode distance. Additional details on this type of tracking technique can be found in U.S. Pat. No. 5,983,126, entitled "Catheter Location System and Method", which is expressly and fully incorporated herein by reference.

3. Imaging Element Locator

The imaging element locator 60 determines the current geometry of the imaging device 20 and the position and/or orientation of the imaging element 25 in the 3-D coordinate system. In the case where multiple location elements are distributed along the imaging device 20, the imaging element locator 60 can derive the position and/or orientation of the imaging element 25 from the geometry of the imaging device 20. The geometry can be determined by extrapolating the determined positions of the location elements 30 in the 3-D coordinate system based on the known structure of the imaging device 20 and positional relationship between the location elements 30. The position and orientation of the imaging element 25 in the 3-D coordinate system can then be determined given the current geometry of the imaging device 20 and the relative location of the imaging element 25 on the imaging device 20. The structure of the imaging device 20, arrangement of the location elements 30, and the position and orientation of the imaging element 25 relative to the imaging device 20 may be preprogrammed into the imaging element locator 60 for the case in which the imaging element 25 is in a fixed position relative to one or more of the location elements 30. This information may also be entered into the imaging element locator 60 by a user, e.g., physician, using a user interface, e.g., keyboard.

It should be noted that if imaging element locator 60 does not calculate the geometry of the imaging device 20 and the orientation of the imaging element 25, a single location element 30 can be placed in close proximity to the imaging element 25, so that the position of the location element 30 approximates the position of the imaging element 25. In the case where the magnetically-based location tracking system 55(2) is used to determine the location of a location element 30(2) (which obtains orientation information), however, the orientation of the imaging element 25 can be determined based on the orientation information acquired by the location element 30(2).

Alternatively, if the location tracking subsystem 55 is ultrasound-based, the position of the imaging element 25 can be determined by using the imaging element 25, itself, as an ultrasound location element. Specifically, the imaging element 25 can be operated in two different resonant modes that are associated with different frequencies, e.g., 9 MHz and 1 MHz. That is, the imaging element 25 can be operated in one resonant mode at 9 MHz to generate ultrasound imaging pulses, and can be operated in a second resonant mode at 1 MHz to generate ultrasound positioning pulses. The imaging element 25 can be conveniently operated in these two resonant modes by stimulating it with a single electrical pulse that exhibits harmonic frequencies corresponding to the resonant modes. The relatively short pulsewidth of the electrical pulses used to stimulate the imaging element 25 during the imaging function naturally contain harmonic frequencies that can stimulate both resonant modes of the imaging element 25. This technique is advantageous in that it compensates for any axial shifting ("creep") of the imaging element 25 relative to the catheter body. That is, because the imaging element 25 is being used to track itself, the positional coordinates of the imaging element 25, however axially shifted, can be accurately determined. Further details on this technique are disclosed in copending U.S. patent application Ser. No. 10/318,571 (now U.S. Pat. No. 6,719,700), entitled "Ultrasound Ranging For Localization of Imaging Element," which is fully and expressly incorporated herein by reference.

In many cases, the location elements 30 will not move relative to the imaging element 25, and thus the relative positions therebetween will not vary over time. For the pull-back embodiment of the imaging device 20(1a) illustrated in FIG. 3A, however, the relative position of the imaging element 25(1a) (i.e., ultrasound imaging transducer) varies. In this case, the relative position of the imaging element 25 may be determined by displacing the imaging element 25(1a) axially within the catheter body 315 to the distal end of the catheter body 315. The relative position of the distal end of the catheter body 315 is typically known and fixed relative to one or more of the location elements 30 (not shown in FIG. 3A) on the imaging device 20(1). Once the imaging element 25(1a) is at the distal end of the catheter body 315, the imaging element 25(1a) may be pulled back from the distal end by a certain distance. The relative position of the imaging element 25(1a) may then be determined by subtracting the distance that the imaging element 25(1a) is pulled back from the distal end of the catheter body 315 from the relative position of the distal end to one or more of the location elements 30.

In the embodiment of FIG. 3A, one of the location elements 30 may alternatively be attached (not shown) to the imaging element 25(1a) or the drive shaft 330 carrying the imaging element 25(1a) such that the location element 30 remains in a fixed position relative to the imaging element 25(1a). The position of the imaging element 25(1a) may then be determined using the tracked position of the location element 30 and the fixed relative position of the imaging element 25(1a) to the location element 30.

4. The Imaging Pattern Subsystem

The image pattern generator 70 generates a graphical representation of the imaging device's 20 imaging pattern. Parameters for generating the graphical representation of the imaging pattern include the scan pattern of the imaging element 25 from the imaging device 20. In the illustrative example of FIG. 3A, the imaging element 25(1a) scans the body by rotating about the axis 340 of the imaging device 20(1a). Relative to the rotational axis 340, the imaging element 25(1a) looks to the side at an angle of $\phi$. This produces a scan pattern that sweeps out a conical surface having a centerline aligned with the axis 340 of the imaging device 20(1a). Another parameter is the range or depth of penetration of the imaging element 25 in the body. For an ultrasound imager, the range is determined by the maximum time-delay (i.e., round trip time) of the back-reflected ultrasound pulses (echoes) and the rate of energy absorption in the tissue, as is well known in the art. The range of an ultrasound imager is typically from a few millimeters to a few inches. For an optical imager, the range of penetration of the light may be determined by the wavelength and phases of the back-reflected light, as is well known in the art. In the illustrative example of FIG. 3A, the range of the imaging element 25(1a) is represented graphically as a line 345 extending from the imaging element 25(1a) to a range of r. The range r value may be readily determined from the image depth of the interior image taken by the imaging device 20.

Figure 8A:
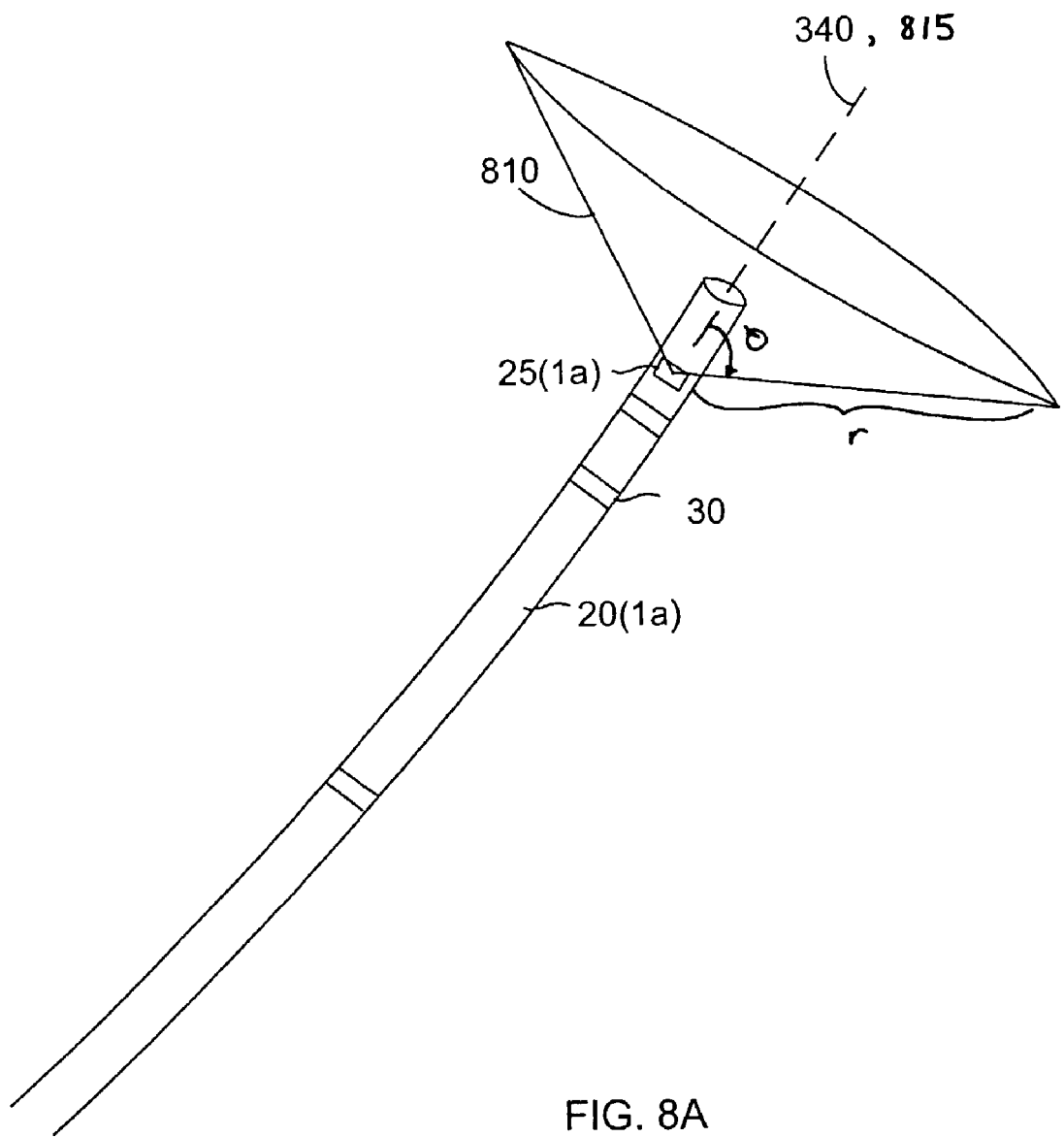
FIG. 8A is a plan view of a graphical representation of a typical imaging pattern for the ultrasonic imaging device of FIG. 3A.

The imaging pattern subsystem 70 generates a graphical representation of the imaging pattern based on the scan pattern of the imaging element 25 at a range of r. FIG. 8A illustrates the imaging pattern 810 associated with the imaging device 20(1a) of FIG. 3A. The imaging pattern 810 has a conical shape resembling a flattened martini glass that radiates outwardly in the forward direction from the location of the imaging element 25(1a) at an angle of $\phi$ and a range of r. In addition, the centerline 815 of the imaging pattern 810 is aligned with the axis 340 of the imaging device 20(1a). This is because the imaging element 25(1a) in this particular example scans the interior of the body by rotating about the axis 340 of the imaging device 20(1a).

Note that in this and any other case, the imaging pattern need not be represented as a static solid object. For imaging systems that use mechanical motion or electronical scanning of the imaging element 25, the imaging pattern 810 can be depicted as the real-time (or time-adjusted) representation of the actual scanning of the imaging element 25.

Figure 8B:
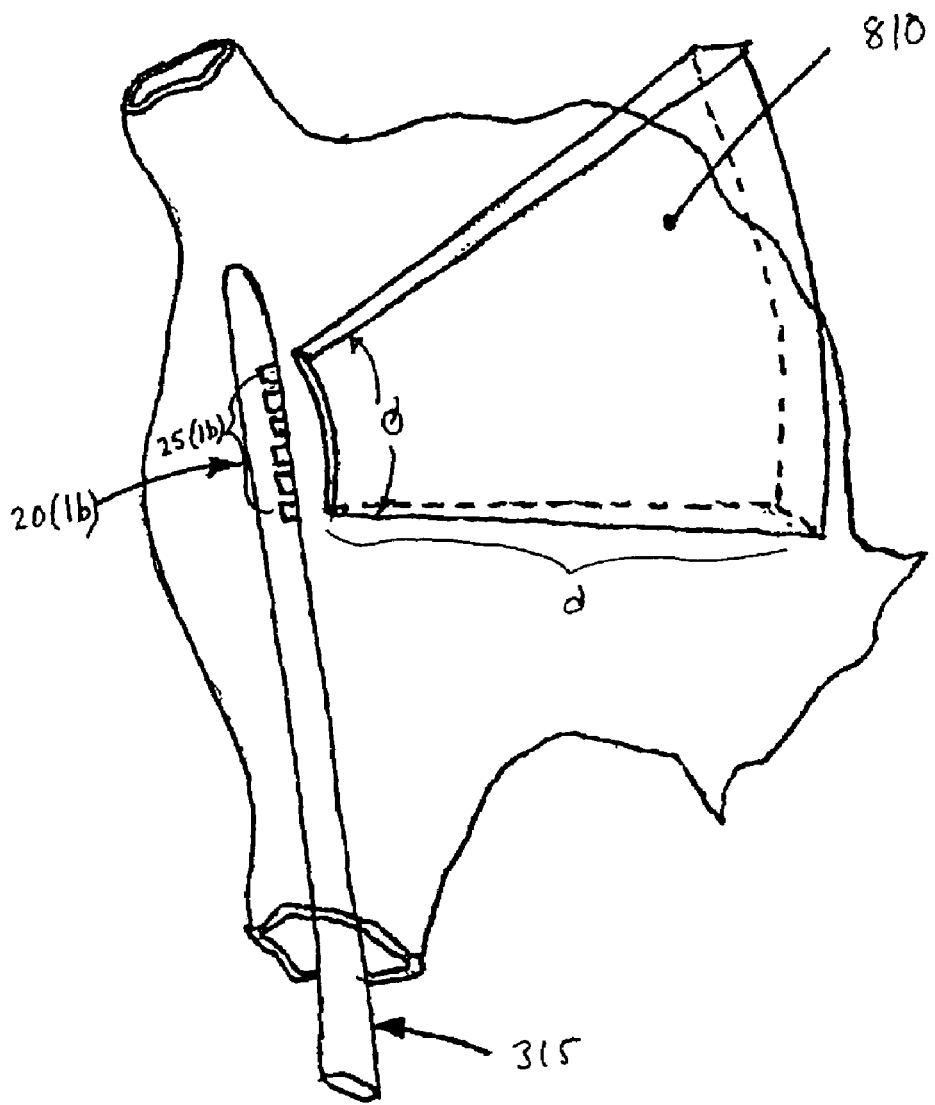
FIG. 8B is a plan view of a graphical representation of a typical imaging pattern for the ultrasonic imaging device of FIG. 3B.
Figure 8C:
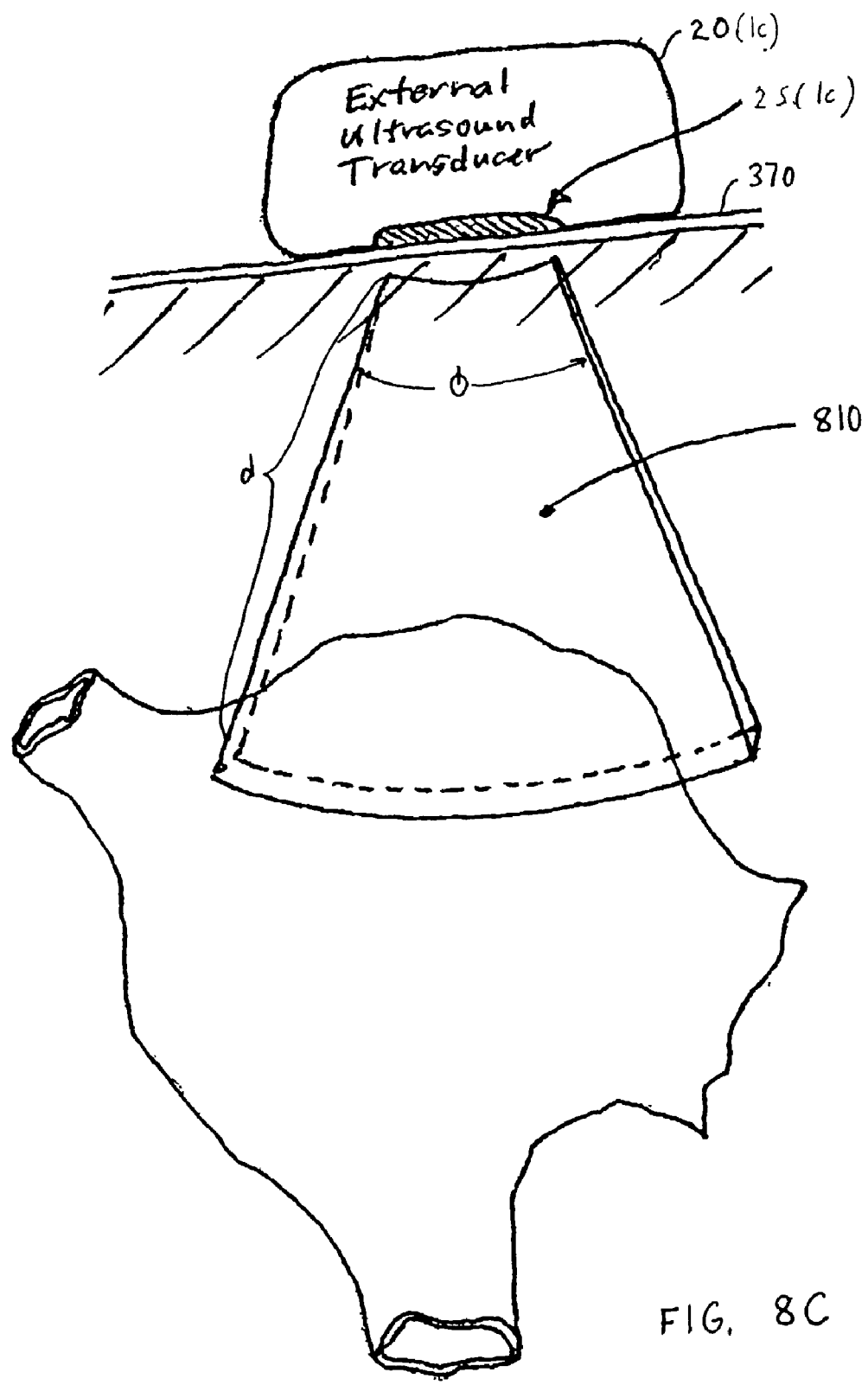
FIG. 8C is a plan view of a graphical representation of a typical imaging pattern for the ultrasonic imaging device of FIG. 3C.

FIG. 8B illustrates the imaging pattern 810 associated with the phased transducer array 25(1b) of FIG. 3B. The phased array 25(1b) scans a sector of the body producing a sector-shaped imaging pattern 810. The angular extent $\phi$ and the focal depth d of the imaging pattern 810 can be controlled by individually controlling the phase or delay of each of the transducers of the array 25(1b), e.g., using delay elements. FIG. 8C illustrates the imaging pattern 810 associated with the external transducer array 25(1c) of FIG. 3C.

Figure 8D:
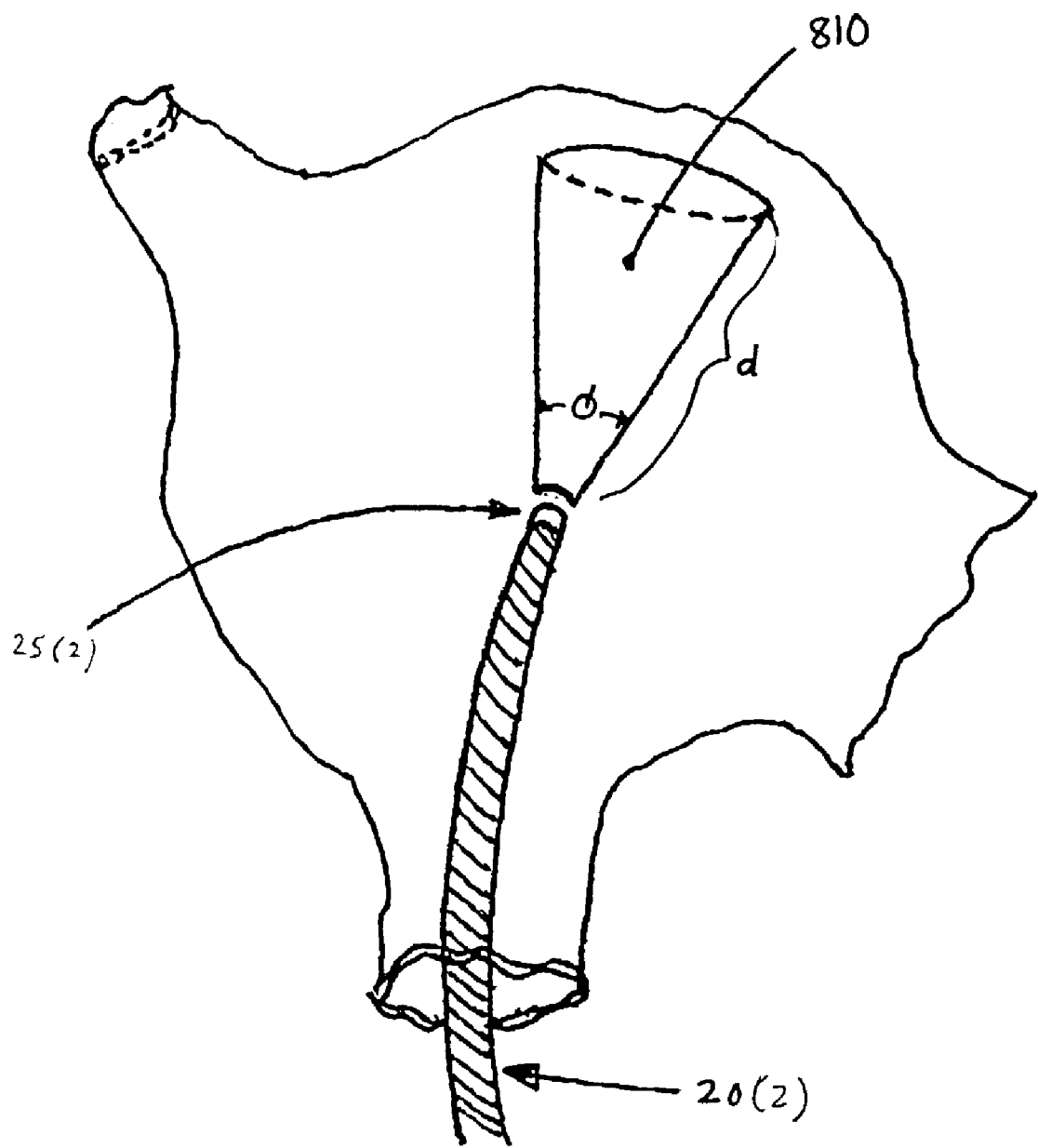
FIG. 8D is a plan view of a graphical representation of a typical imaging pattern for the optical imaging device of FIG. 4.

FIG. 8D illustrates the imaging pattern associated with the optical imaging catheter 20 of FIG. 4. The imaging lens 25(2) of the optical imaging catheter 20(2) projects the light from the optical fiber 420 in a conical pattern producing a conical shaped imaging pattern 810. The angular width or viewing angle $\phi$ of the lens 25(2), and therefore of the imaging pattern 810, is determined by the construction of the lens 25(2). For example, a wide-angle lens 25(2) may be used for applications requiring a wide viewing angle φ, and a telephoto lens 25(2) may be used for application requiring a narrow viewing angle φ.

5. The Global Representation Device

Figure 9:
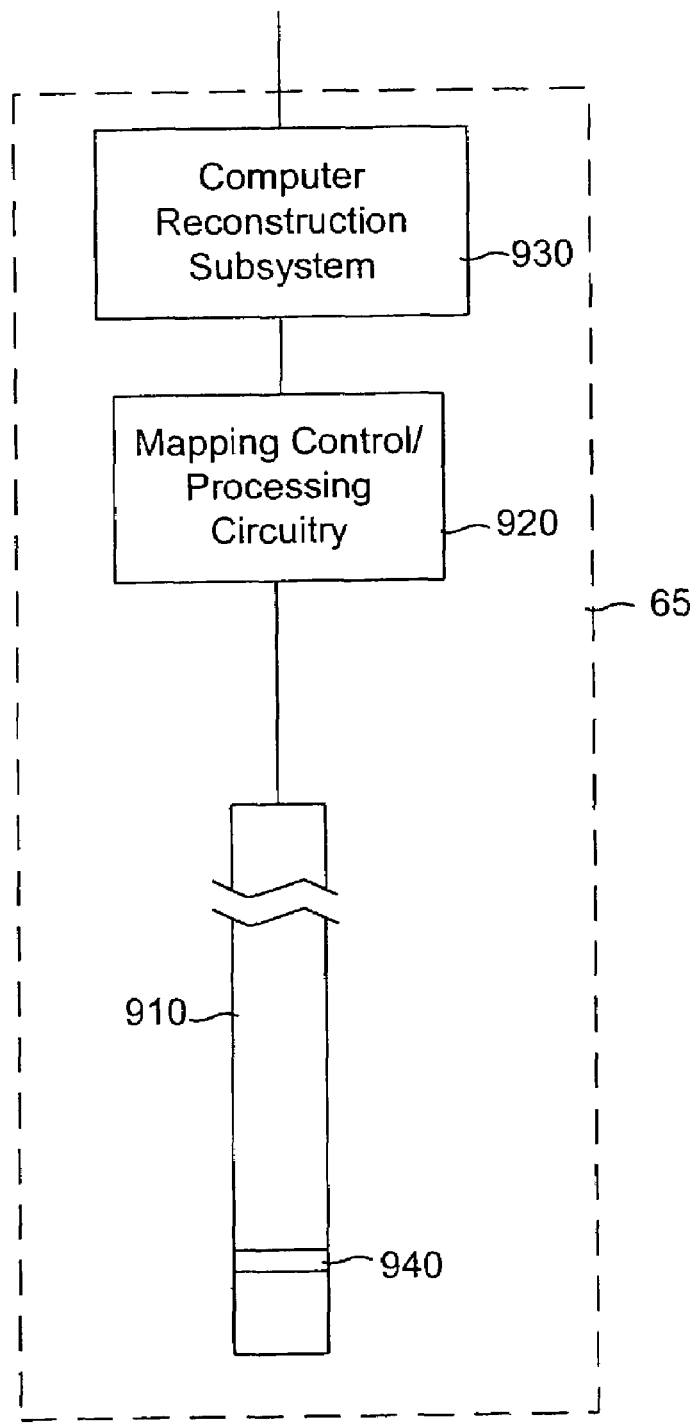
FIG. 9 is a functional block diagram of a graphically-based global representationr that can be used with the body tissue imaging system of FIG. 1.

FIG. 9 shows an embodiment of the global representation device 65 that generates a global representation of the body in the form of a computer-generated representation (i.e., reconstruction) of the body tissue, e.g., a heart chamber, within which the imaging device 20 is to be guided and/or the imaging pattern of the imaging device 20 is to be depicted. The global representation device 65 includes a mapping device 910, mapping control/processing circuitry 920 coupled to the mapping device 910, and a computer reconstruction subsystem 930 coupled to the mapping control/processing circuitry 920. The mapping device 910 further includes one or more location element(s) 940 for tracking the position of the mapping device 910 in the 3-D coordinate system established by the reference element 50 (not shown in FIG. 9). The location elements 940 may employ any one of the tracking techniques described above for tracking the position of the imaging device 20.

Figure 10:
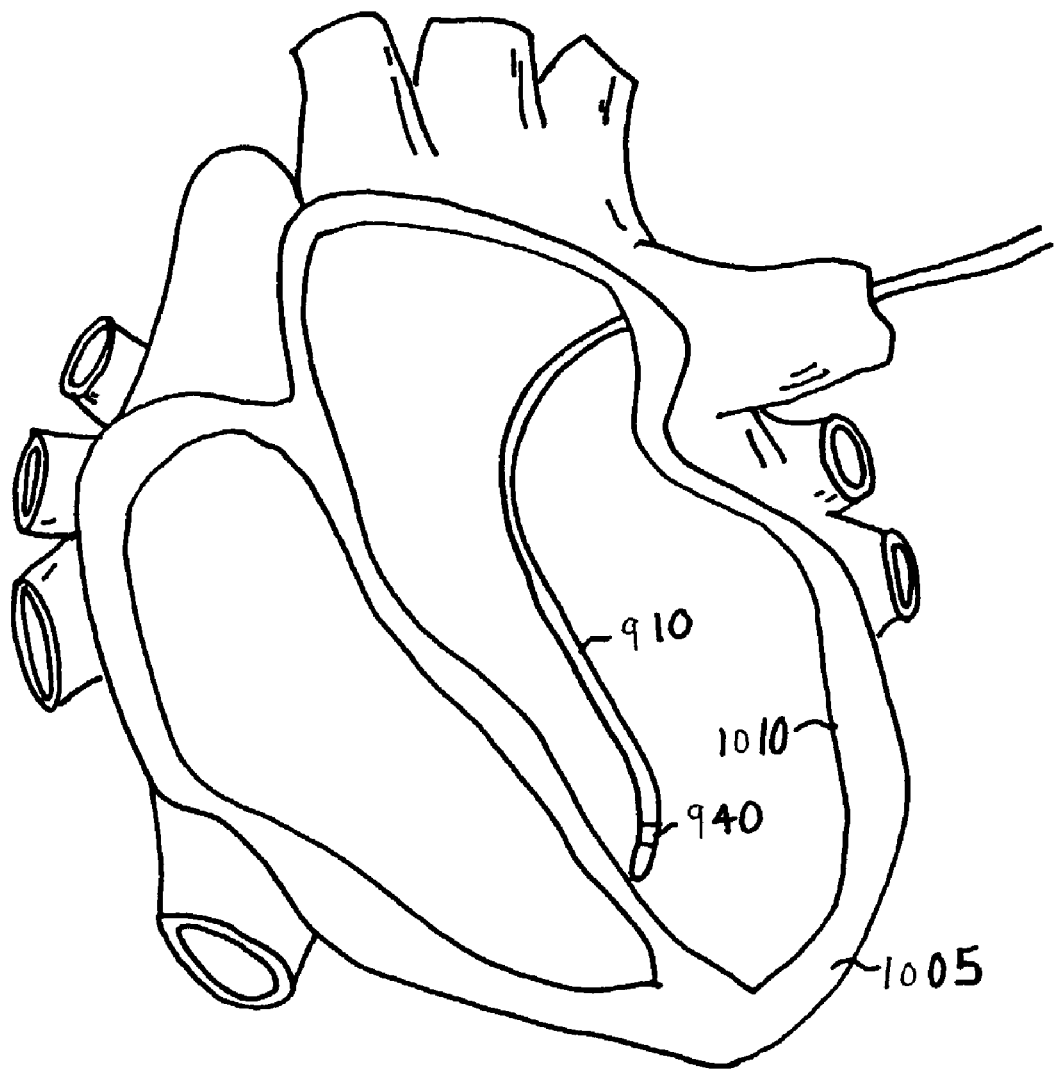
FIG. 10 is a plan view illustrating the use of the graphically-based global representationr of FIG. 9 in mapping a patient's heart.

The operation of the global representation device 65 according to this embodiment will be described with reference to FIG. 10 using the example of a heart chamber 1010. It should be appreciated that other body tissues can be graphically represented such as the esophagus, uterus, and the like. The mapping device 910 is inserted into the heart chamber 1010 in order to structurally map the inner wall of the heart chamber 1010 in the 3-D coordinate system. The mapping device 910 is moved to different locations on the inner wall of the heart chamber 1010. At each location of the heart chamber 1010, the mapping control/processing circuitry 920 maps the location of the heart chamber 1010 in the 3-D coordinate system. Mapping the locations of the heart chamber 1010 with respect to the 3-D coordinate system enables the mapped locations to be registered with the 3-D coordinate system. To reduce the effects of cardiac motion of the heart on the mapping process, the position of each location may be acquired at the same phase in the cardiac cycle of the heart. This may be accomplished by gating the position acquisition times of the mapping control/processing circuitry 920 with an electrocardiogram (EKG) monitor that is monitoring the cardiac cycle of the heart. After the heart chamber 1010 has been mapped, the mapping control/processing circuitry 920 outputs the mapped locations of the heart chamber 1010 to the computer reconstruction subsystem 930 in order to reconstruct a 3-D computer representation of the heart chamber 1010. The reconstruction subsystem 930 does this by mapping the locations of the heart chamber 1010 in the 3-D coordinate system and fitting an anatomical shell onto the mapped locations using graphical techniques known in the art. The resulting 3-D computer-generated representation of the heart chamber 1010 provides a computer reconstruction of the geometry of the heart wall. In addition, the 3-D computer-generation of the heart chamber 1010 is registered with the 3-D coordinate system since the mapped locations used to reconstruct the hear chamber 1010 are taken with respect to the 3-D coordinate system. The 3-D representation of the heart 1010 chamber may be stored in memory (not shown) for later. Those skilled in the art with appreciate that the imaging device 20 may be adapted to perform the mapping function since it is also equipped with location elements 30. This would eliminate the need to provide a separate mapping device 930. In addition, the tracking control/processing circuitry 52 may be adapted to perform the functions of the mapping control/processing circuitry 920. Additional details on this graphical reconstruction technique can be found in U.S. patent application Ser. No. 08/905,090, entitled "System for Electrode Localization Using Ultrasound," and U.S. patent application Ser. No. 09/128,304, entitled "A dynamically alterable three-dimensional graphical model of a body region," which have previously been incorporated herein by reference.

Figure 11:
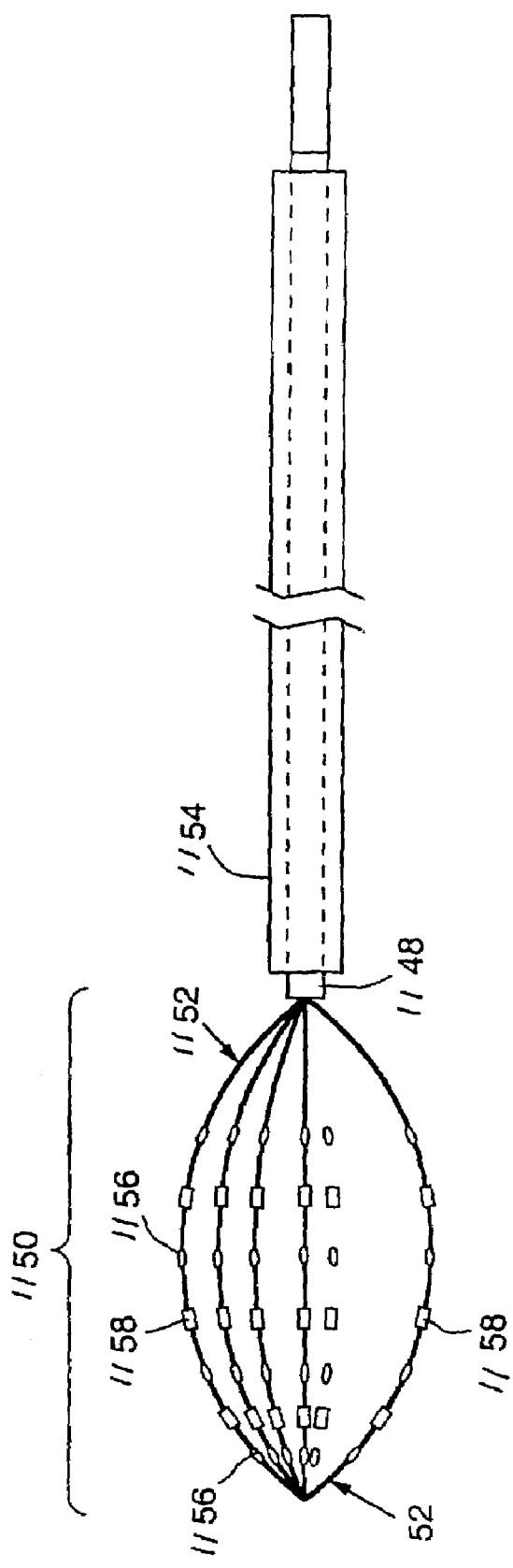
FIG. 11 is a plan view of an electrical activity mapping device that may be used in the body tissue imaging system of FIG. 1.

In should be noted that the mapping device 930 may include electrodes for mapping the electrical activity of the heart chamber 1010 as well as mapping the structure of the heart chamber 1010. An example of such a mapping device is shown in FIG. 11. The mapping device in FIG. 11 has a "basket" structure 1150 at its distal end. The basket structure 1150 comprises a plurality of arms 1152, in which each arm has electrodes 1156 and ultrasound transducers 1158 alternately disposed thereon. The arms 1152 are preferably made of a resilient material that is able to bend along the contours of the heart chamber 1010 wall. The ultrasound transducers 1158 track positions on the heart chamber 1010 in the 3-D coordinate system using ultrasound-based tracking. The electrodes 1156 measure the electrical activity of the heart chamber 1125 at the positions determined by the ultrasound transducers 1158. The mapping subsystem 930 may use the electrical measurements to map the electrical activity of the heart chamber 1010, which can be overlaid onto the computer-generated representation of the heart chamber 1010 to show the electrical pattern of the heart chamber 1010. Knowledge of the electrical activity of the heart chamber 1010 may be especially useful in the treatment of cardiac arrhythmia to identify ablation sites in the heart chamber 1010. Additional details on the construction and operation of the mapping device in FIG. 11 can be found in U.S. Pat. No. 6,216,027, entitled "Systems for Electrode Localization Using Ultrasound", which is expressly and fully incorporated herein by reference.

Instead of or in addition to graphically reconstructing the body tissue, the global representation device 65 may employ any one of a number of imaging techniques to generate a 3-D image of the body tissue. For example, the global representation device 65 may comprise a Magnetic Resonance Imaging (MRI) imager, a Computed Tomography (CT) imager, an optical imager, and/or ultrasonic imager (all not shown) to generate a 3-D image of a body tissue. To accomplish this, the imager may be moved laterally and/or rotationally to obtain multiple cross-sectional or sector images of the body tissue at different positions within the body tissue. The global representation device 65 may then aggregate (i.e., piece together) the multiple cross-sectional images to reconstruct a 3-D image of the body tissue. The 3-D image of the body tissue may be registered with the 3-D coordinate system by tracking the position of the imager, and therefore the cross-sectional or sector images taken by the imager, in the 3-D coordinate system using any one of the above-described tracking techniques. For example, ultrasound location transducers or magnetic location arrays may be attached to the imager and/or a device carrying the image for tracking the position of the imager in the 3-D coordinate system. Alternatively, the position of anatomic landmarks within the body tissue may be determined in the 3-D coordinate system, e.g., using a mapping device 910. The 3-D image of the body tissue may then be registered with the 3-D coordinate system by correlating the positions of the anatomic landmarks in the 3-D image of the body tissue with the determined positions of the anatomic landmarks in the 3-D coordinate system.

6. The Composite Image Generator

The composite image generator 75 produces a composite image comprising a graphical representation of the imaging device 20 and its imaging pattern within the global representation of the body.

Figure 12:
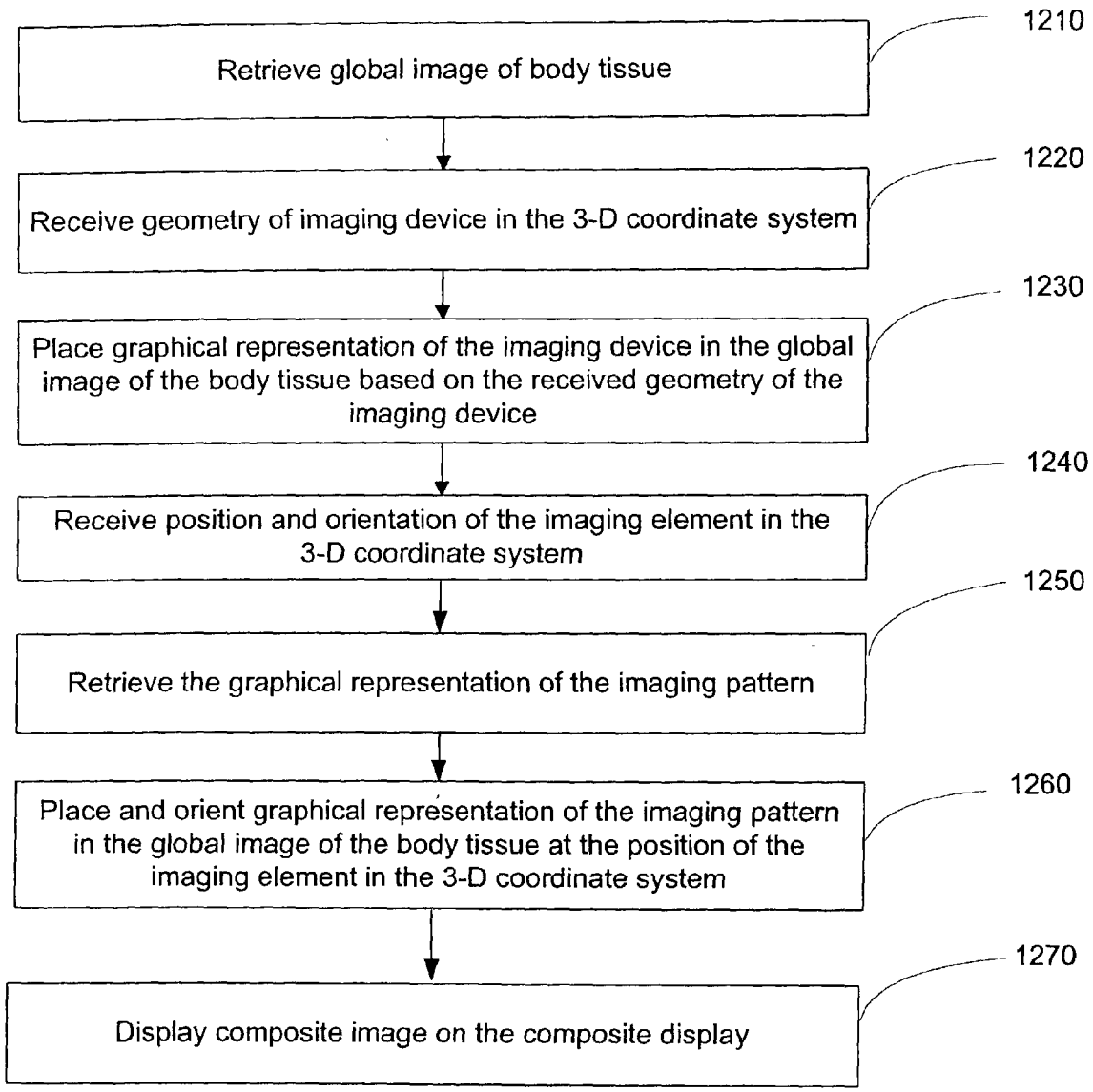
FIG. 12 is a flowchart illustrating steps performed by a composite image generator used in the body tissue imaging system of FIG. 1.

Processing steps of the composite image generator 75 according to one embodiment will be described with reference to FIG. 12. It is to be understood that that the specific ordering and combination of steps described in FIG. 12 is merely illustrative, and that the invention can be performed using a different combination or ordering of the steps.

In step 1210, the composite image generator 75 retrieves the global representation of the body tissue from the global representation device 65. In step 1220, the composite image generator 75 receives the geometric positions of the imaging device 20 from the imaging element locator 70. In step 1230, the composite image generator 75 places a graphical representation of the imaging device 20 within the global representation of the body tissue based on the geometric positions. To accomplish this, the composite image generator 75 fits a pre-programmed 3-D graphical representation of the imaging device 20 onto the coordinates of the geometric positions. Because the global representation of the body tissue is registered with the 3-D coordinate system, the graphical representation of the imaging device 20 is placed in the correct position and orientation within the global representation of the body tissue.

In step 1240, the composite image generator 75 receives the position and orientation of the imaging element 25 in the 3-D coordinate system from the image element locator 60. In step 1250, the composite image generator 75 retrieves the graphical representation of the imaging pattern from the image pattern generator 70. In step 1260, the composite image generator 75 positions the graphical representation of the imaging pattern within the global representation of the body tissue at the coordinates, i.e., position, of the imaging element 25 in the 3-D coordinate system. In addition, the composite image generator 75 properly orientates the graphical representation of the imaging pattern 810 within the global representation of the body tissue and the imaging device 20. For the example, illustrated in FIG. 8A, the centerline 815 of the imaging pattern 810 is aligned with the axis 340 the imaging device 20.

In step 1270, the composite image generator 75 displays the composite image on the composite image display 80. The graphical representation of the imaging device 20 in the composite image indicates the position and orientation of the imaging device 20 in relation to the global representation of the body tissue. This enables a physician to maneuver and guide the imaging device 20 to a site of interest within the body tissue. Furthermore, the graphical representation of the imaging pattern 810 provides a visual indication of the portion of the body being imaged by the imaging device 20 in relation to the global representation of the body tissue. This enables the physician to confirm that the imaging device 20 is imaging a site of interest within the body tissue and to better understand the portion of the body tissue that he or she is imaging with the imaging device 20.

Figure 13A:
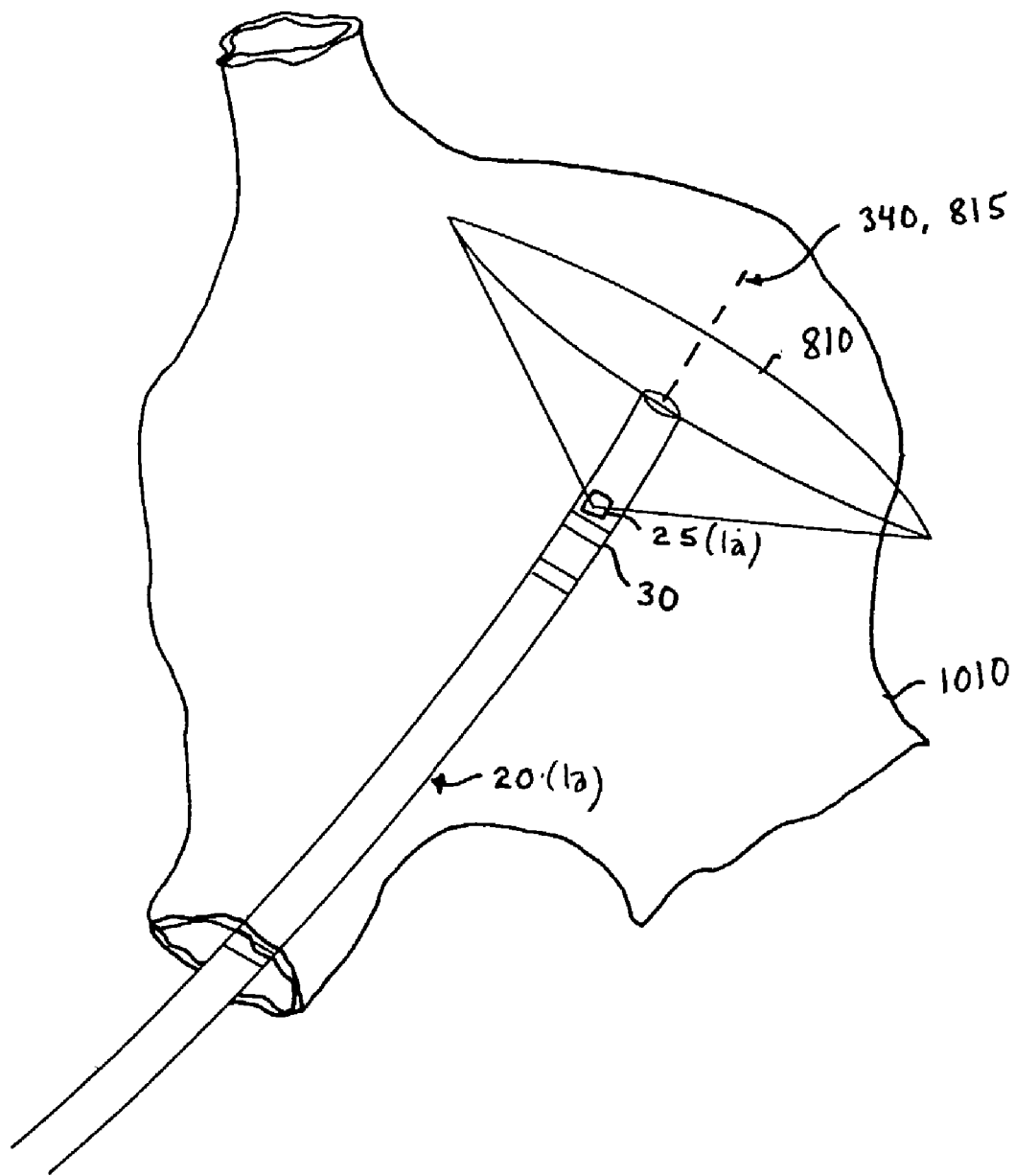
FIG. 13A is a plan view of one composite image that can be generated by the composite image generator of FIG. 12 based on the use of the ultrasonic imaging device of FIG. 3A within the heart.
Figure 13:
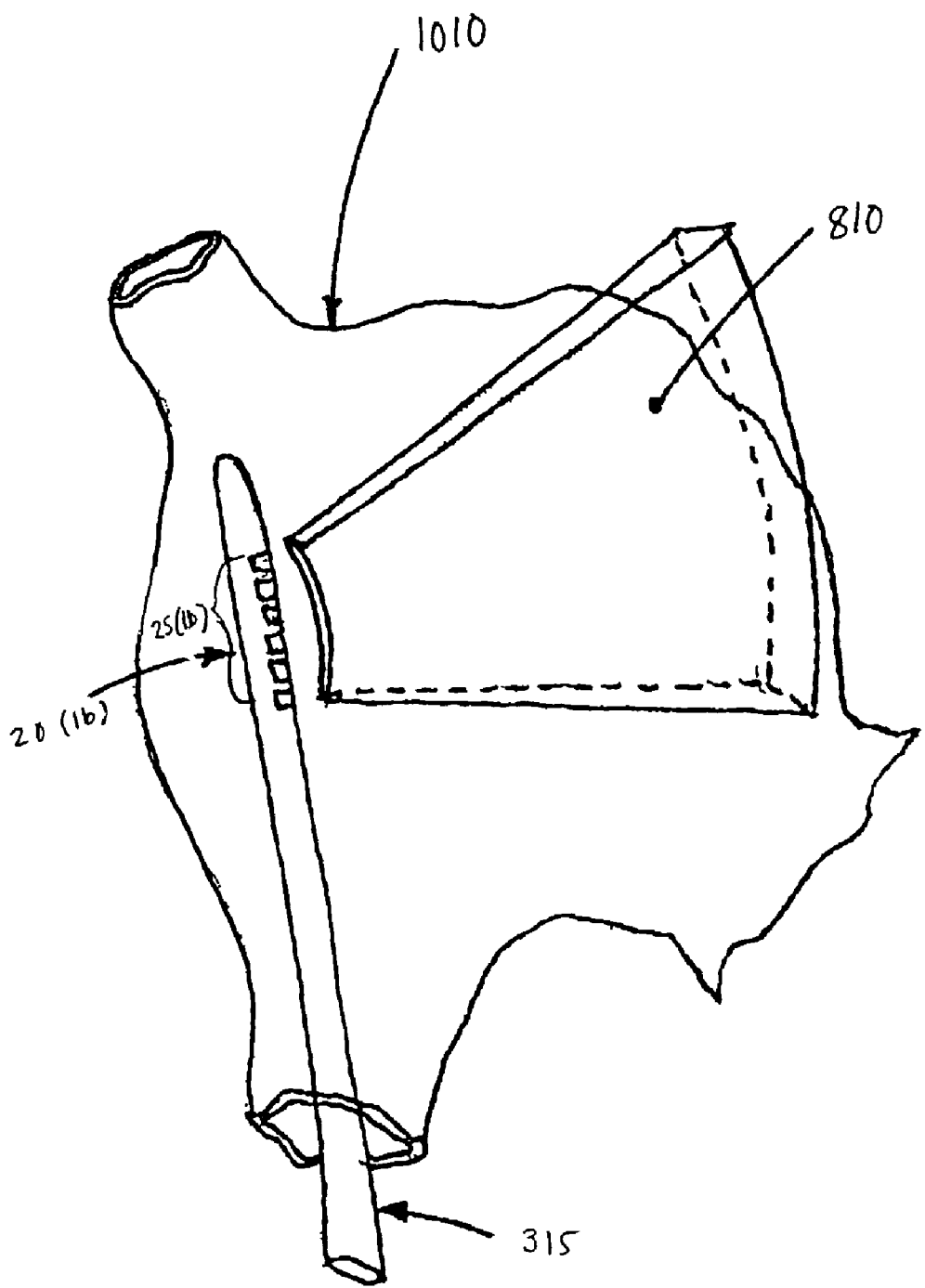
FIG. 13B is a plan view of another composite image that can be generated by the composite image generator of FIG. 12 based on the use of the ultrasonic imaging device of FIG. 3B within the heart.
FIG. 13C is a plan view of still another composite image that can be generated by the composite image generator of FIG. 12 based on the use of the ultrasonic imaging device of FIG. 3C (located outside of the heart, but with its imaging pattern intersecting the heart)
FIG. 13D is a plan view of still another composite image that can be generated by the composite image generator of FIG. 12 based on the use of the optical imaging device of FIG. 4 within the heart.

FIG. 13A illustrates an exemplary composite image showing a graphical representation of the imaging device 20(1*a*) of FIG. 3A and its associated imaging pattern 810 in global representation of a heart chamber 1010. The graphical representation of the imaging device 20(1*a*) indicates the position and orientation of the imaging device 20(1*a*) within the heart chamber 1010. In this example, the graphical representation of the imaging device 20(1*a*) includes graphical representations of the imaging element 25(1*a*) and the location elements 30. The composite image display 80 further shows the graphical representation of the imaging device's imaging pattern 810. In the example, the graphical representation of the imaging pattern 810 has a conical shape and radiates outwardly in the forward direction from the position of the imaging element 25(1*a*). In addition, the centerline 815 of the graphical representation of the imaging pattern 810 is aligned with the axis 340 of the graphical representation of the imaging device 20(1*a*).

Figure 13C:
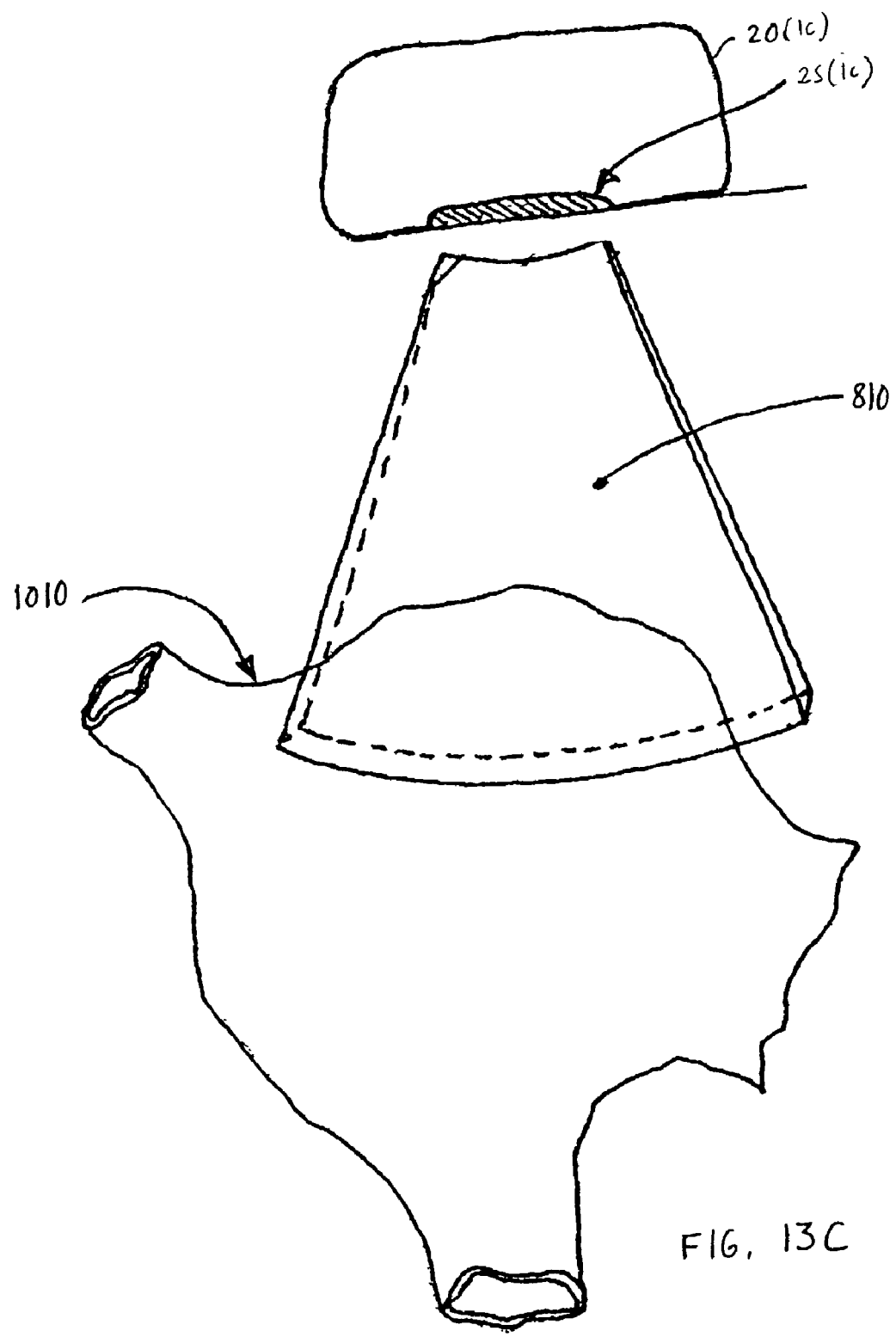
Figure 13D:
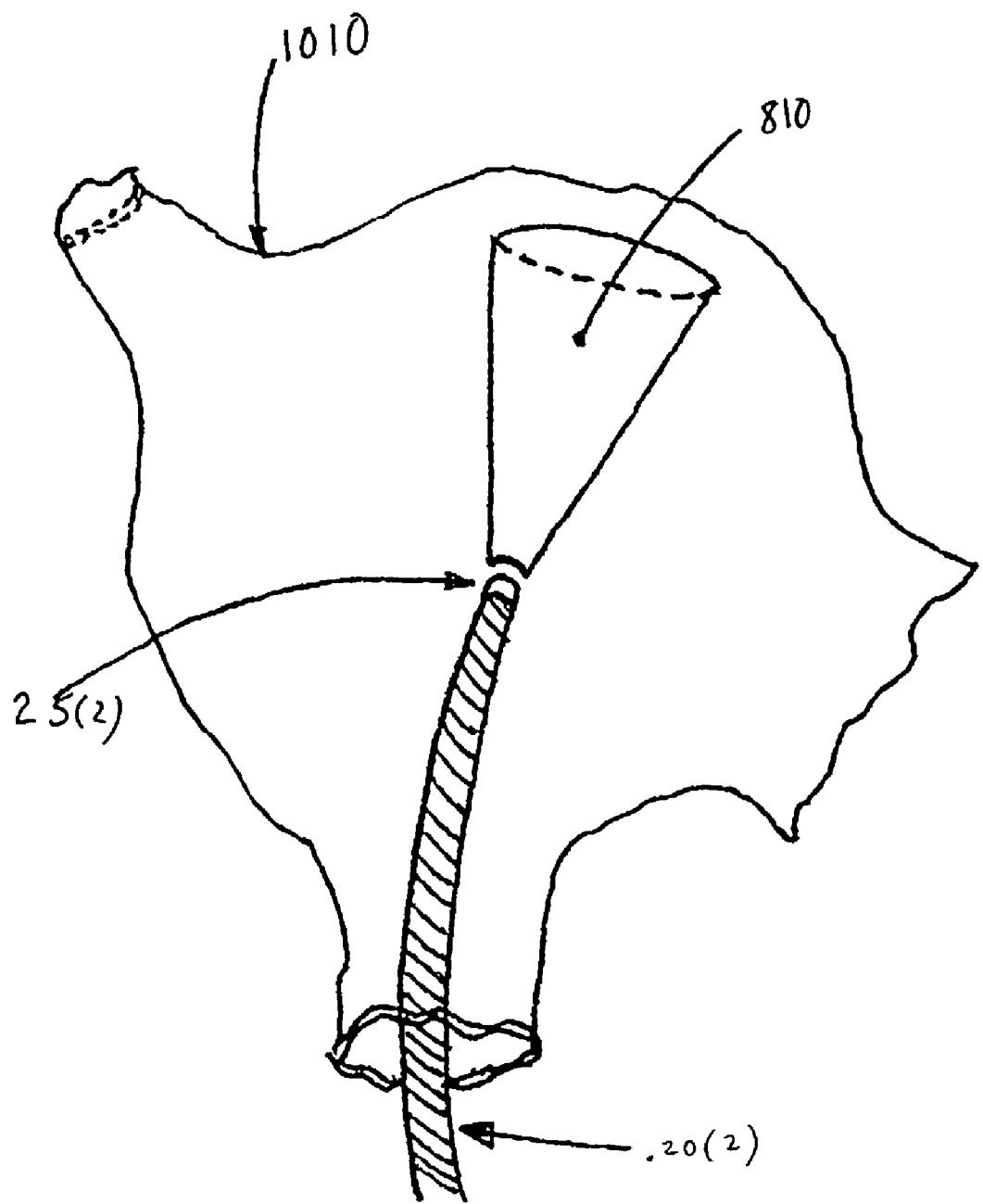

FIG. 13B and illustrate an exemplary composite image showing the graphical representation of the imaging device 20(1*b*) of FIG. 3B and its associated imaging pattern 810 in the global representation of the heart chamber 1010. FIG. 13C and illustrate an exemplary composite image showing the graphical representation of the imaging device 20(1*c*) of FIG. 3B and its associated imaging pattern 810 in the global representation of the heart chamber 1010. In each of the two examples above, the imaging pattern 810 is sectored-shaped. FIG. 13D illustrates a composite image showing the graphical representation of the optical imaging device 20(2) of FIG. 4 and its associated imaging pattern in the global representation of the heart chamber 1010. In this example, the imaging pattern 810 has a conical shape that radiates outwardly in the forward direction from the imaging lens 25(2).

The graphical representation of the imaging pattern 810 provides a visual indication of the portion of the heart chamber 1010 being imaged by the imaging device 20 in relation to the global representation of the heart chamber 1010. In addition, the graphical representation of the imaging pattern enables the physician to reference the interior image of the heart chamber 1010 shown on the local image display 40 to the corresponding portion of the global representation of the heart chamber 1010.

Figure 14:
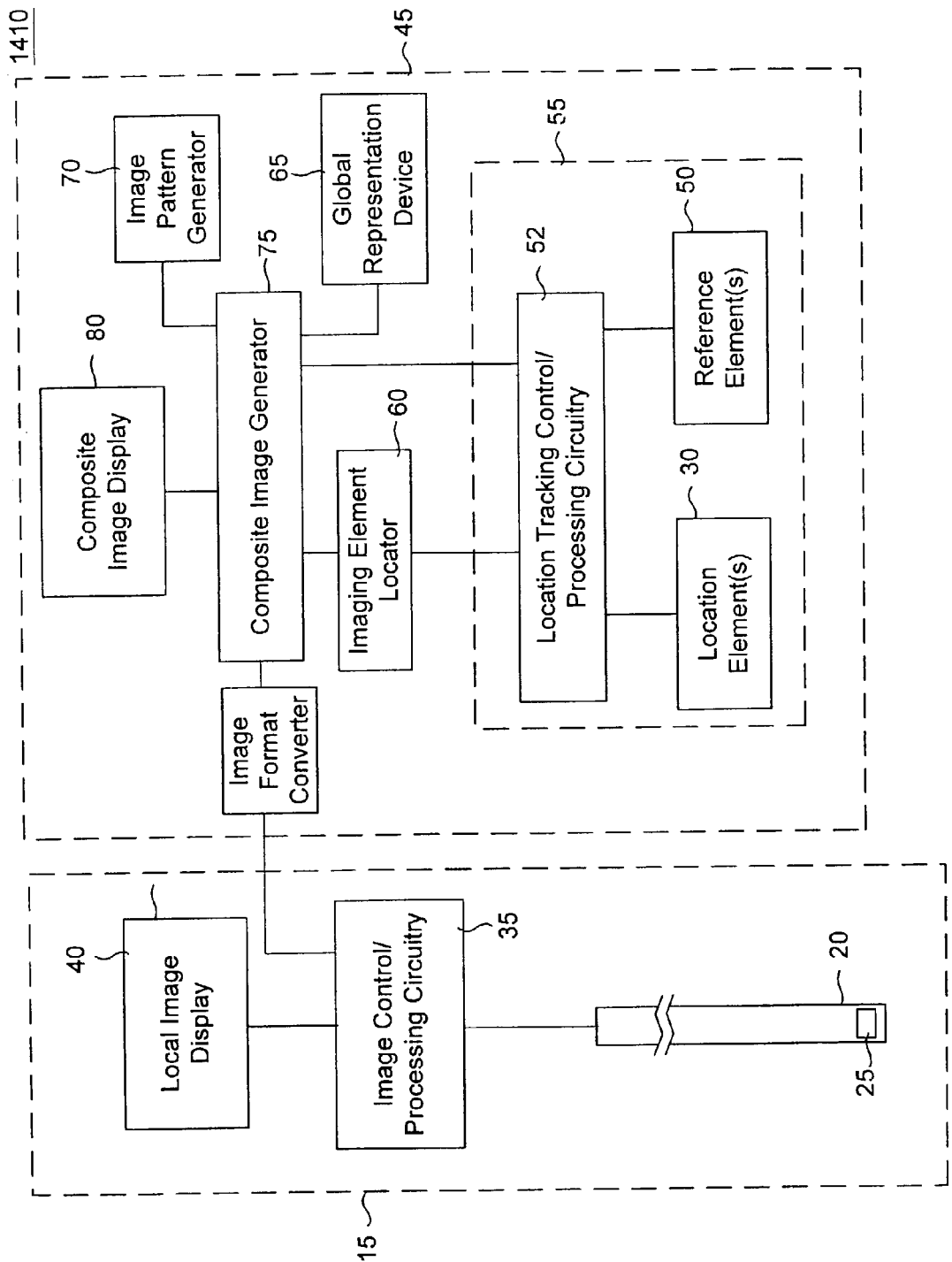
FIG. 14 is a functional block diagram of another preferred embodiment of a body tissue imaging system constructed in accordance with the present inventions.

In another embodiment of the system 1410 illustrated in FIG. 14, the composite image generator 75 is coupled to the image control/processing circuitry 35 for receiving local interior images taken by the imaging device 20. The system 1410 may optionally include an image format converter 1415 when the image control/processing circuitry 35 and the image composite generator 75 use different image formats. In this case, the image format converter 1415 converts the local interior images from the image control/processing circuitry 35 into an image format that is suitable for processing by the image composite generator 75.

The composite image generator 75 according to this embodiment is able to display both the received local interior and the composite image on the composite image display 80. The guidance subsystem 45 may give the user, e.g., the physician, the option of displaying the local interior image and the composite image simultaneously on the composite image display 80. This option enables the user to more easily reference the local interior image to the corresponding portion of the global representation of the body.

In addition, the composite image generator 75 may map the local interior image onto the surface of the graphical imaging pattern. For a two-dimensional (2-D) local interior image, the composite image generator 75 may perform the mapping procedure using commercially available OpenGL-based graphical software, e.g., developed by Xi Graphics, Inc., capable of mapping the 2-D local image onto a 3-D surface of the imaging pattern. This mapping procedure is commonly referred to as "textual mapping".

Preferably, the roll of the imaging element is determined in order to properly orient the local image onto the graphical imaging pattern. For example, in the case of a non-rotating imaging element (such as, e.g., transducer arrays 25(1*b*) or (1*c*) or optical imaging lens 25(2)), sensors that are capable of acquiring information relating to the roll of the imaging element (such as, e.g., the magnetic location array 30(2) of the location tracking subsystem 55(2)), can be mounted adjacent the imaging element, so that the roll of the imaging element can be tracked.

Alternatively, in the case of rotating ultrasound imaging element 25(1a), an ultrasound transducer mounted in a known location within the three-dimensional coordinate system, such as on the patient's body or on another catheter located in proximity to the imaging element 25(1a), can be used to transmit ultrasound signals to the imaging element 25(1a). The received ultrasound signals result in a second distinct image or artifact within the local image, which provides an indication of the rotational orientation of the local image relative to the known reference transducer location. This information can then be used to reorient the local image. Further details on this technique can be found in U.S. Pat. No. 6,248,075, which is hereby expressly incorporated herein by reference.

Alternatively, an ultrasound transducer can be located on another catheter and be configured to receive ultrasound energy from the imaging element 25(la) as the imaging beam intersects the transducer. Or an ultrasound transducer, whether located on another catheter or somewhere else, can receive ultrasound energy from a separate ultrasound transducer located on the distal end of the drive shaft 330 adjacent the imaging element 25(1a). The ultrasound energy transmitted by this separate ultrasound transducer exhibits a broad out-of-plane beamwidth, such that there is a high likelihood that the receiving ultrasound transducer will receive the transmitted ultrasound energy. In either case, an incremental relative rotational orientation of the imaging element 25(1a) can then be correlated with the time segment that the ultrasound transducer receives the ultrasound energy from the imaging element 25(1a) or otherwise broad beamwidth transmitting ultrasound transducer. Given a position of the receiving ultrasound transducer relative to the body organ that is being imaged, the local image can be reoriented based on the calculated rotational orientation of the imaging element 25(1a). The receiving ultrasound transducer can serve as a location element 30, or a location element 30 can be placed on the catheter a known distance from the receiving ultrasound transducer, so that the relative position of the ultrasound transducer can be determined. Further details on this technique can be found in U.S. patent application Ser. No. 10/319, 285, entitled "Method and Apparatus for Orienting a Medical Image," which is hereby expressly incorporated herein by reference.

An exemplary mapping procedure will now be given with reference to FIGS. 15A-15C using the example of the local imaging device 20(1a) of FIG. 3A and the corresponding conically-shaped imaging pattern 810 of FIG. 8A.

Figure 15A:
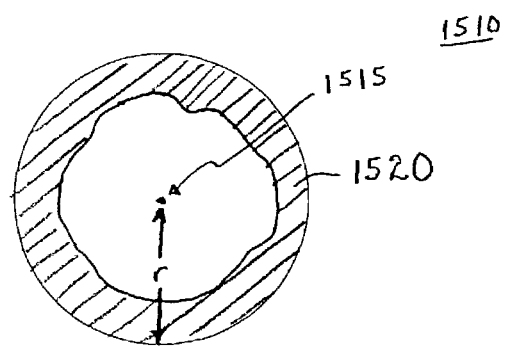
FIG. 15A is a plan view of an exemplary local interior image taken with the imaging device of FIG. 3A.

FIG. 15A shows an exemplary local interior image 1510 taken with the local imaging device 20(1a) of FIG. 3A. The local image 1510 is a circular two-dimensional image produced by rotating the ultrasound imaging element 25(1a) of the imaging device 20(1a) 360 degrees. The center 1515 of the local image 1510 corresponds to the position of the imaging element 25(a1) and the radius, r, of the local image 1515 corresponds to the range of the image. In this example, the local interior image 1510 depicts body tissue 1520, e.g., a heart chamber wall.

Figure 15B:
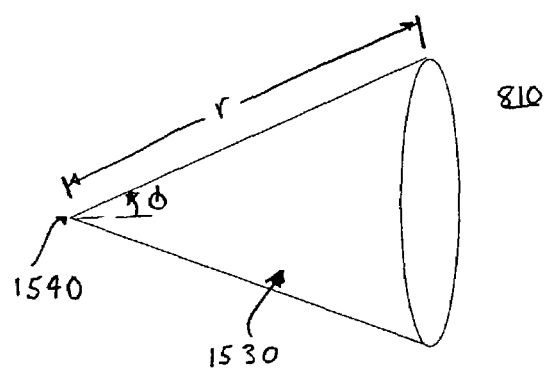
FIG. 15B is a plane view of a conically-shaped imaging pattern associated with the imaging device of FIG. 3A.

FIG. 15B shows the conically-shaped imaging pattern 810 onto which the local image 1510 is to be mapped. The conical imaging pattern 810 has a side surface 1530 with a length corresponding to the range, r, of the image 1510. The tip 1540 of the conical imaging pattern 810 corresponds to the position of the imaging element 25(1a), and the angle φ is the scanning angle of the imaging element 25(1a) with respect to the rotational axis 340 of the imaging element 25(1a).

Figure 15C:
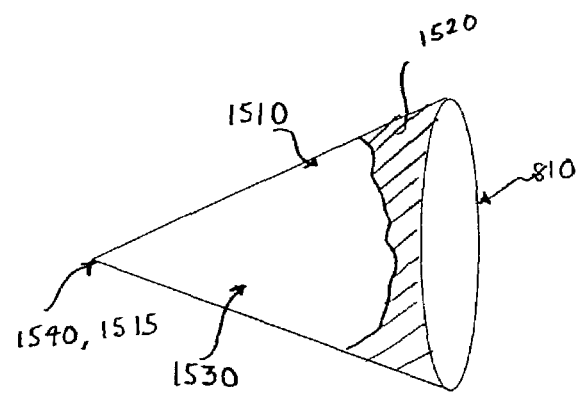
FIG. 15C is a plane view of the local interior image of FIG. 15A mapped onto the surface of the imaging pattern of FIG. 15B.

FIG. 15C illustrates the local interior image 1510 mapped onto the imaging pattern 810. In this case, the local interior image 1510 is mapped onto the side surface 1530 of the conically-shaped imaging pattern 810.

In yet another embodiment, the composite image generator 75 produces and displays an image that shows the portion of the global representation of the body that intersects the imaging pattern. The resulting intersection image enables the user to directly compare the local interior image with the corresponding portion of the global representation of the body.

In the foregoing description, the graphical representation of the imaging pattern was displayed in a global representation in the form of a 3-D image or computer representation of the body. For less demanding applications that do not require precise guiding of the imaging device 20, the graphical representation of the image pattern may be displayed in a 2-D image or computer representation of the body, such as the image obtained using fluoroscopy.

Figure 16:
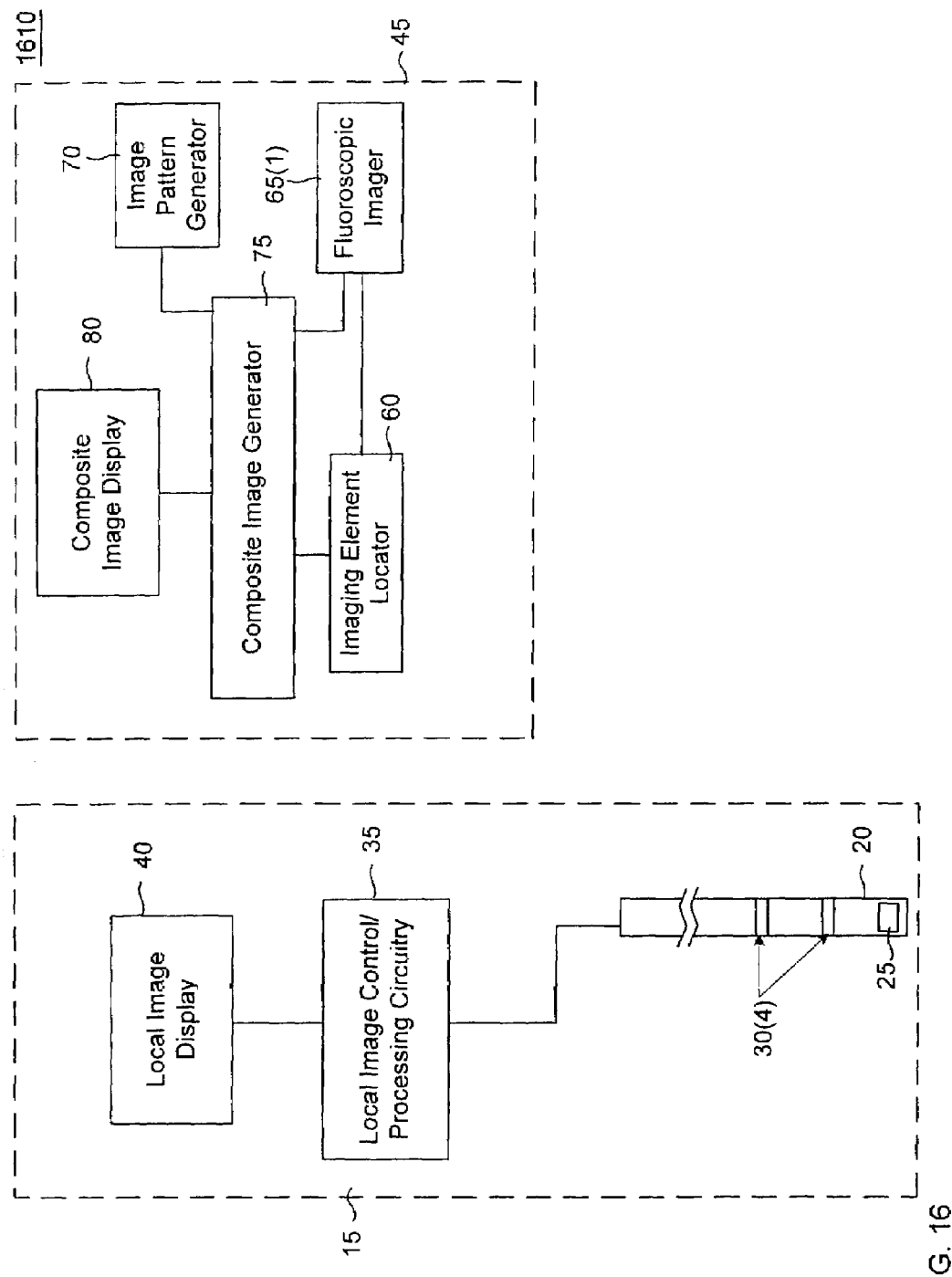
FIG. 16 is a functional block diagram of still another preferred embodiment of a body tissue imaging system constructed in accordance with the present inventions.

FIG. 16 illustrates an embodiment of the system 1610 of the invention that uses fluoroscopy to image the portion of the body within which the imaging device 20 is to be guided. In this embodiment, the location element(s) 30 takes the form of one or more radiopaque markers 30(4) located on the imaging device 20 and/or reference devices and the global representation device 65 takes the form of a fluoroscopic (i.e., x-ray) imager 65(1). The imaging element 25 is preferably at a known position relative to the radiopaque markers 30(4) and the fluoroscopic imager 65(1) is coupled to the image element locator 60. Note that this embodiment does not include the tracking control/processing circuitry 52 and the reference element 50.

To guide the imaging device 20 in the body, the fluoroscopic imager 65(1) is used to directly image the imaging device 20 as well as the surrounding body tissue. The fluoroscopic imager 65(1) outputs the fluoroscopic image to the composite image generator 75 and the imaging element locator 60. Because the fluoroscopic image already includes an image of the imaging device 20, a graphical representation of the imaging device 20 is not required. The imaging element locator 60 determines the position and orientation of the imaging element 25 in the fluoroscopic image based on the position of the radiopaque markers 30(4) in the fluoroscopic image and the known relative position of the imaging element 25 to the radiopaque markers 30(4). For example, the imaging element locator 60 may then determine the position and orientation of the imaging device 20 by connecting line segments between the radiopaque markers 30(4) in the fluoroscopic image. The connecting line segments provide a two-dimensional estimation of the orientation of the imaging device 20 in the fluoroscopic image.

The imaging element locator 60 outputs the determined position and orientation of the imaging element 25 to the composite image generator 75. The composite image generator 75 produces a composite image comprising the fluoroscopic image of the imaging device 20 and surrounding body tissue, and a 2-D graphical representation of the imaging pattern associated with the imaging device 20. The composite image generator 75 positions the graphical representation of the imaging pattern within the composite image at the determined position of the imaging element 25 given by the imaging element locator 60. The composite imaging generator 75 also properly orients the graphical representation of the imaging pattern relative to the determined orientation of the imaging device 20 in the fluoroscopic image.

In the foregoing specification, the invention has been described with reference to a specific embodiment thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, features known to those of skill in the art can be added to the embodiment. Other processing steps known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A body tissue imaging system, comprising:
a local imaging device having an imaging pattern for use in generating a local image of the body tissue, the image pattern representing the volume of energy emitted from the local imaging device;
a global representation device configured for generating a global representation of the body tissue; and
a composite image generator in communication with the global representation device and configured for generating a composite image comprising the global representation and a graphical representation of a shape of the imaging pattern derived independently from the local image.

2. The imaging system of claim 1, wherein the imaging device comprises one or more imaging elements from which the imaging pattern originates, the imaging system further comprising an imaging element locator configured for locating the one or more imaging elements relative to the global representation, wherein the composite image generator is configured for positioning the graphical imaging pattern within the composite image based on the determined location of the one or more imaging elements.

3. The imaging system of claim 2, wherein the imaging element locator is configured for determining the orientation of the one or more imaging elements relative to the global representation, and the composite image generator is further configured for orienting the graphical imaging pattern within the composite image based on the determined location of the one or more imaging elements.

4. The imaging system of claim 2, further comprising one or more locating elements disposed on the local imaging device, wherein the imaging element locator is configured for locating the one or more imaging elements based on the locations of the one or more locating elements.

5. The imaging system of claim 4, wherein the one or more locating elements comprises a single locating element adjacent the one or more imaging elements.

6. The imaging system of claim 4, wherein the one or more locating elements comprises a plurality of locating elements displaced along the local imaging device.

7. The imaging system of claim 4, further comprising location tracking control/processing circuitry configured for determining the locations of the one or more locating elements in a three-dimensional coordinate system.

8. The imaging system of claim 4, wherein the image element locator is configured for determining the locations of the one or more locating elements in the context of the global representation.

9. The imaging system of claim 1, further comprising a global display in communication with the composite image generator, the display configured for displaying the composite image.

10. The imaging system of claim 1, wherein the local imaging device is an internal imaging device.

11. The imaging system of claim 1, wherein the local imaging device is an external imaging device.

12. The imaging system of claim 1, wherein the imaging pattern is conically-shaped.

13. The imaging system of claim 1, wherein the imaging pattern is sector-shaped.

14. The imaging system of claim 1, wherein the global representation device comprises a standard imaging device.

15. The imaging system of claim 1, wherein the global representation device comprises a graphical image generator.

16. The imaging system of claim 1, wherein the global representation device is configured for generating an image of the imaging device within the context of the global representation.

17. The imaging system of claim 1, further comprising local imaging control/processing circuitry in communication with the local imaging device for generating the local image.

18. The imaging system of claim 17, further comprising a local display in communication with the local imaging control/processing circuitry, the local display configured for displaying the local image.

19. The imaging system of claim 17, wherein the composite image generator is in communication with the local imaging control/processing circuitry, and the global display is configured for displaying the local image.

20. The imaging system of claim 1, further comprising memory for storing the graphical representation of the imaging pattern.

21. The imaging system of claim 20, wherein the graphical representation of the imaging pattern is pre-stored in the memory.

22. The imaging system of claim 1, further comprising a graphical image pattern generator for generating the graphical representation of the imaging pattern.

23. A method for imaging body tissue, comprising:
generating a local image of the body tissue with an imaging pattern of a local imaging device, the imaging pattern representing the volume of energy emitted from the local imaging device;
generating a global representation of the body tissue; and
generating a composite image comprising the global representation and a graphical representation of a shape of the imaging pattern derived independently from the local image.

24. The method of claim 23, further comprising:
locating an origin of the imaging pattern; and
positioning the graphical imaging pattern within the composite image based on the determined location of the imaging pattern origin.

25. The method of claim 24, further comprising:
determining an orientation of the imaging pattern;
orienting the graphical imaging pattern within the composite image based on the determined orientation of the imaging pattern.

26. The method of claim 23, wherein the body tissue is locally imaged internally.

27. The method of claim 23, wherein the body tissue is locally imaged externally.

28. The method of claim 23, wherein the imaging pattern is conically-shaped.

29. The method of claim 23, wherein the imaging pattern is sector-shaped.

30. The method of claim 23, wherein the global representation is a standard image.

31. The method of claim 23, wherein the global representation is a graphical image.

32. The method of claim 23, wherein the imaging pattern is associated with a local imaging device, the method further comprising generating an image of the local imaging device, wherein the global composite image comprises the image of the local imaging device.

33. The method of claim 23, wherein the graphical representation is a three-dimensional representation.

34. The method of claim 23, further comprising storing the graphical representation of the imaging pattern.

35. The method of claim 34, wherein the graphical representation of the imaging pattern is pre-stored prior to local image is generated.

36. The method of claim 23, further comprising generating the graphical representation of the imaging pattern.

37. A body tissue imaging system, comprising:
means for generating a local image of the body tissue with an imaging pattern, the imaging pattern representing the volume of energy emitted from the local image generating means;
means for generating a global representation of the body tissue; and
means for generating a composite image comprising the global representation and a graphical representation of a shape of the imaging pattern derived independently from the local image.

38. The system of claim 37, further comprising:
means for locating an origin of the imaging pattern; and
means for positioning the graphical imaging pattern within the composite image based on the determined location of the imaging pattern origin.

39. The system of claim 38, further comprising:
means for determining an orientation of the imaging pattern;
means for orienting the graphical imaging pattern within the composite image based on the determined orientation of the imaging pattern.

40. The system of claim 37, further comprising means for generating an image of the local imaging device, wherein the global composite image comprises the image of the local imaging device.

41. The system of claim 1, wherein the graphical representation is a three-dimensional representation.

42. The method of claim 37, wherein the graphical representation is a three-dimensional representation.

43. The system of claim 37, further comprising means for storing the graphical representation of the imaging pattern.

44. The system of claim 43, further comprising means for the pre-storing the representation of the imaging pattern prior to local image is generated.

45. The system of claim 37, further comprising means for generating the graphical representation of the imaging pattern.

* * * * *